US007750012B2

(12) United States Patent
Sandanayaka et al.

(10) Patent No.: US 7,750,012 B2
(45) Date of Patent: Jul. 6, 2010

(54) BIARYL NITROGEN-HETEROCYCLE INHIBITORS OF LTA4H FOR TREATING INFLAMMATION

(75) Inventors: Vincent Sandanayaka, Northboro, MA (US); Jasbir Singh, Naperville, IL (US); Li-Ming Zhou, Hinsdale, IL (US); Mark E. Gurney, Grand Rapids, MI (US)

(73) Assignee: deCODE genetics ehf, Reykjavik (IS)

( * ) Notice: Subject to any disclaimer, the term of this patent is extended or adjusted under 35 U.S.C. 154(b) by 34 days.

(21) Appl. No.: 11/462,278

(22) Filed: Aug. 3, 2006

(65) Prior Publication Data

US 2007/0149544 A1    Jun. 28, 2007

Related U.S. Application Data

(60) Provisional application No. 60/752,273, filed on Dec. 21, 2005.

(51) Int. Cl.
| A61K 31/495 | (2006.01) |
| A61K 31/496 | (2006.01) |
| C07D 295/15 | (2006.01) |
| C07D 333/16 | (2006.01) |
| A61K 31/5375 | (2006.01) |
| A61K 31/5377 | (2006.01) |
| A61K 31/451 | (2006.01) |
| A61K 31/4523 | (2006.01) |
| C07D 211/34 | (2006.01) |
| C07D 211/58 | (2006.01) |
| C07D 413/12 | (2006.01) |

(52) U.S. Cl. ............... 514/252.13; 514/255.03; 514/231.5; 514/239.2; 514/317; 514/329; 514/331; 544/146; 544/174; 544/379; 544/391; 544/394; 546/223; 546/224; 546/239

(58) Field of Classification Search .......... None
See application file for complete search history.

(56) References Cited

U.S. PATENT DOCUMENTS

| 4,064,245 | A | * | 12/1977 | Beregi et al. ............ 514/255.03 |
| 4,210,646 | A | | 7/1980 | Janssen |
| 2005/0043378 | A1 | | 2/2005 | Axe et al. |

FOREIGN PATENT DOCUMENTS

| EP | 0328268 | 8/1989 |
| EP | 0412899 | 2/1991 |
| EP | 0755923 | 1/1997 |
| EP | 0757986 | 2/1997 |
| EP | 1650206 | 4/2004 |
| EP | 0630954 | 12/2004 |
| EP | 1555267 | 7/2005 |
| GB | 1489711 | 10/1977 |
| JP | 59090863 | 5/1984 |
| JP | 5043550 | 2/1993 |
| JP | 2000149320 | 5/2000 |
| WO | 8905803 | 6/1989 |
| WO | WO9322303 | 11/1993 |
| WO | WO9910344 | 3/1999 |
| WO | WO9916751 | 4/1999 |
| WO | WO0026192 | 5/2000 |
| WO | WO0066566 | 11/2000 |
| WO | WO0149681 | 7/2001 |
| WO | WO0164645 | 9/2001 |
| WO | WO0179170 | 10/2001 |
| WO | WO0187870 | 11/2001 |
| WO | WO0248117 | 6/2002 |
| WO | WO02074767 | 9/2002 |
| WO | WO02085903 | 10/2002 |
| WO | WO03000688 | 1/2003 |
| WO | WO03062234 | 7/2003 |
| WO | WO2005007672 | 1/2005 |
| WO | WO2005014563 | 2/2005 |
| WO | WO2005056015 | 6/2005 |
| WO | WO2005120509 | 12/2005 |
| WO | WO2006066747 | 6/2006 |

OTHER PUBLICATIONS

Sakai, K. et al. "Synthesis of 3-Substituted Pyrrole Derivatives with Anti-inflammatory Activity". Chem. Pharm. Bull, vol. 28, No. 8, 1980, pp. 2384-2393.

Miller, J.A. et al. "Nickel Catalyzed Cross-Coupling and Amination Reactions of Aryl Nitriles". Synthesis, No. 11, 2003, pp. 1643-1648.

Takenaka, S. et al. "The thermal properties of liquid crystalline materials incorporating a piperazine skeleton", Bulletin of the Chemical Society of Japan, vol. 58, No. 3, pp. 1079-1080 (1985).

(Continued)

*Primary Examiner*—Emily Bernhardt
(74) *Attorney, Agent, or Firm*—Heslin Rothenberg Farley & Mesiti P.C.

(57) ABSTRACT

The present invention relates to a chemical genus of biaryl nitrogen-attached heterocycles that are inhibitors of LTA4H (leukotriene A4 hydrolase). The compounds have the general formula

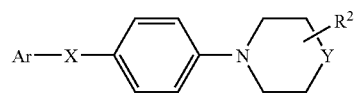

They are useful for the treatment and prevention and prophylaxis of inflammatory diseases and disorders.

23 Claims, No Drawings

OTHER PUBLICATIONS

Huang, Y. et al. "Synthesis of Potent and Selective Dopamine D4 Antagonists as Candidate Radioligands". Bioorg & Med. Chemistry Letters, No. 11, 2001, pp. 1375-1377.

Matulenko, M. et al. "Synthesis and activity of 2-[4-(4-[$^3$H]-2-cyanophenyl) piperazinyl]-$N$-(2,4,6-[$^3$H]$_3$-3-methylpheny)acetamide: a selective dopamine $D_4$ receptor agonist and radioligand", Bioorg & Med. Chemistry Letters, No. 14, 2004, pp. 5095-5098.

Wilson, W. D. et al. "The interaction with DNA of unfused aromatic systems containing terminal piperazino substituents". Biophysical Chemistry, vol. 35, No. 2-3, 1990, pp. 227-243.

Deligeorgiev, T. G. "An improved method for the preparation of 2-Aryl-, 2-Hetaryl- and 2-Styrylbenzothiazoles". Dyes and Pigments, vol. 12, No. 4, 1990, pp. 243-248.

Kubota, Y. et al. "Synthesis of novel benzimidazole dyes and their binding mode to DNA", Nucleic Acids Symposium Series, vol.—, No. 35, 1996, pp. 151-152.

A. J. Pearson et al. J. Org. Chem., vol. 59, No. 16, 1994, pp. 4561-4570.

J.A. Kiritsy et al. J. Med. Chem., vol. 21, No. 12, 1978, pp. 1301-1307.

Database Registry Chem Abstracts Service XP002449302—Jul. 10, 2001.

Database Chemcats Chem Abstracts XP002413309—Aurora Screening Library, May 10, 2006.

Database Chemcats Chem Abstracts XP002413310—Aurora Screening Library, May 10, 2006.

Database Registry Chem Abstracts XP002449299—Aurora Fine Chemicals, Jul. 28, 2006.

Database Registry Chem Abstracts XP002449300—Aurora Fine Chemicals, Jul. 28, 2006.

International Search Report and Written Opinion for International Application No. PCT/US2006/030525. 2007.

* cited by examiner

BIARYL NITROGEN-HETEROCYCLE INHIBITORS OF LTA4H FOR TREATING INFLAMMATION

CROSS-REFERENCE TO RELATE APPLICATION

This application claims priority from U.S. Provisional Application Ser. No. 60/752,273, filed Dec. 21, 2005, the entire contents of which are incorporated herein by reference.

FIELD OF THE INVENTION

The present invention relates to a chemical genus of biaryl nitrogen-attached heterocycles that are inhibitors of LTA4H (leukotriene A4 hydrolase). They are useful for the treatment and prevention and prophylaxis of inflammatory diseases and disorders.

BACKGROUND OF THE PRESENT INVENTION

The end products of the leukotriene pathway are potent inflammatory lipid mediators derived from arachidonic acid. They can potentially contribute to development of atherosclerosis and destabilization of atherosclerotic plaques through lipid oxidation and/or proinflammatory effects. As described elsewhere, a gene on chromosome 13q12 has been identified as playing a major role in myocardial infarction (MI), [Helgadottir et al., *Nature Genetics* doi:10.1038/ng1311, 8 Feb. 2004]. This gene (ALOX5AP), herein after referred to as an MI disease gene, comprises nucleic acid that encodes 5-lipoxygenase activating protein (FLAP), herein after referred to as FLAP. DNA variants in the FLAP gene increase risk for myocardial infarction by 1.8 fold and for stroke by 1. fold. The leukotriene pathway, through FLAP, leads to the production of leukotriene B4 by the enzyme leukotriene A4 hydrolase (LTA4H). Leukotriene B4 is one of the most potent chemokine mediators of arterial inflammation. Particular DNA variants in the gene encoding LTA4H also elevate risk for MI and stroke, as described elsewhere [Hakonarsson et al., *J. Am. Med. Assoc.* 293, 2245-2256 (2005)]. Individuals with a prior history of MI produce more leukotriene B4 when their isolated neutrophils are stimulated with ionomycin. Increased LTB4 production is particularly marked in male patients with a prior history of MI who carry risk variants in the FLAP gene [Helgadottir et al.]. The treatment (prophylactic and/or therapeutic) of certain diseases and conditions (e.g., MI, acute coronary syndrome (ACS), stroke, atherosclerosis) associated with FLAP or with LTA4H can be accomplished by inhibiting LTA4H. Inhibiting LTA4H is advantageous for methods of treatment for MI or susceptibility to MI; for ACS (e.g., unstable angina, non-ST-elevation myocardial infarction (NSTEMI) or ST-elevation myocardial infarction (STEMI)); for decreasing risk of a second MI; for stroke (including transient ischemic attack) or susceptibility to stroke; for atherosclerosis, such as for patients requiring treatment (e.g., angioplasty, stents, coronary artery bypass graft) to restore blood flow in coronary arteries, such as patients requiring treatment for peripheral vascular disease including peripheral occlusive arterial disease, critical limb ischemia (e.g., gangrene, ulceration), and intermittent claudication to restore blood flow in the lower limbs; for atherosclerotic reno-vascular disease; for abdominal aortic aneurysm; and/or for decreasing leukotriene synthesis (e.g., treatment of MI).

US Patent Application Publication No. 20050043378 and 20050043379, relate to benzooxazol-2-yl, benzothiazol-2-yl and 1H-benzoimidazol-2-yl compounds and derivatives thereof useful as leukotriene A4 hydrolase (LTA4H) inhibitors in treating inflammation and disorders associated with inflammation. These disclosures are incorporated herein by reference as they relate to utility.

SUMMARY OF THE INVENTION

One aspect of the present invention relates to compounds exhibiting LTA4H enzyme inhibition, having general formula:

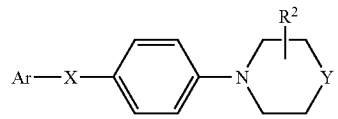

wherein

Ar is selected from the group consisting of aryl, aryl substituted with from one to three substituents independently selected from the group consisting of halogen, loweralkyl, loweracyl, loweralkoxy, fluoroloweralkyl, fluoroloweralkoxy, formyl, cyano, benzyl, benzyloxy, phenyl, heteroaryl, heterocyclylalkyl and nitro; heteroaryl, and heteroaryl substituted with from one to three substituents independently selected from the group consisting of halogen, loweralkyl, loweracyl, loweralkoxy, fluoroloweralkyl, fluoroloweralkoxy, formyl, cyano, sulfonamide, amido, phenyl, heteroaryl, heterocyclylalkyl and nitro;

X is selected from the group consisting of a direct bond, O, $NR^1$, $CH_2$, $OCR^{1a}R^{1b}$ and $CR^{1a}R^{1b}O$;

$R^1$ is selected from the group consisting of H and lower alkyl;

$R^{1a}$ and $R^{1b}$ are selected from the group consisting of H and loweralkyl;

$R^2$ is selected from the group consisting of H, loweralkyl, and —Z—W;

$R^5$ is chosen from H, loweralkyl and —Z—W, with the proviso that both of $R^2$ and $R^5$ are not —Z—W;

Y is chosen from

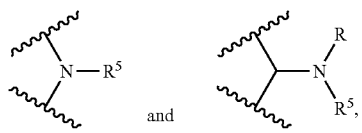

and wherein the wavy lines indicate ring bonds and R is hydrogen or loweralkyl;

Z is $(CH_2)_{1-10}$; in which one or two $(CH_2)$ may optionally be replaced by a $C_3$-$C_6$ carbocycle, a $C_3$-$C_6$ heterocycle, —O—, —$NR^{10}$—, —SO—, —$S(O)_2$—, —C(=O)— or —C=O (NH)—, provided that said —O—, —$NR^{10}$—, —SO—, —$S(O)_2$—, —C(=O)— or —C=O(NH)— are not at the point of attachment to nitrogen and are separated by at least one —$(CH_2)_2$—;

$R^{10}$ is selected from the group consisting of H and lower alkyl

W is selected from acyl, hydroxyl, carboxyl, amino, carboxamido, sulfonamide, aminoacyl, —COOalkyl, —CHO, —C(O)fluoroalkyl, —C(O)$CH_2$C(O)Oalkyl, —C(O)CH$_2$C(O)Ofluoroalkyl, —SH, —C(O)NH(OH), —C(O)N(OH)R$^4$, —N(OH)C(O)OH, —N(OH)C(O)R$^4$, heterocyclyl, substituted aryl, and substituted heterocyclyl; and R$^4$ is selected from the group consisting of H and lower alkyl.

A second aspect of the present invention relates to a pharmaceutical composition comprising a pharmaceutically acceptable carrier and a therapeutically effective amount of a compound described above.

A third aspect of the present invention relates to a method for inhibiting leukotriene A4 hydrolase comprising contacting the LTA4H enzyme with a therapeutically effective amount of a compound described above.

A fourth aspect of the present invention relates to a method for treating a disorder associated with leukotriene A4 hydrolase comprising administering to a mammal a therapeutically effective amount of the compound described above or a salt, hydrate or ester thereof.

DETAILED DESCRIPTION OF THE PRESENT INVENTION

Throughout this specification the substituents are defined when introduced and retain their definitions.

In one aspect the invention relates to biphenyl heterocycle derivatives useful as LTA4H enzyme inhibitors, having the general formula:

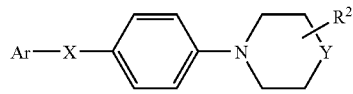

Y is chosen from

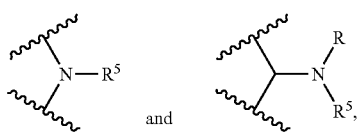

In these representations the wavy lines indicate ring bonds and R is hydrogen or lower alkyl. Examples of the two structures are

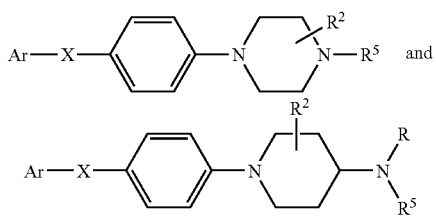

R$^5$ is chosen from H, loweralkyl and —Z—W, with the proviso that both of R$^2$ and R$^5$ are not —Z—W. Z is (CH$_2$)$_{1-10}$ in which one or two (CH$_2$) may optionally be replaced by a C$_3$-C$_6$ carbocycle, a C$_3$-C$_6$ heterocycle, —O—, —NR$^{10}$—, —SO—, —S(O)$_2$—, —C(=O)— or —C=O(NH)—, provided that said —O—, —NR$^{10}$—, —SO—, —S(O)$_2$—, —C(=O)— or —C=O(NH)— are not at the point of attachment to nitrogen and are separated by at least one —(CH$_2$)$_2$—.

Examples where one or two (CH$_2$) linkers of Z are optionally replaced by a C$_3$-C$_6$ carbocycle or a C$_3$-C$_6$ heterocycle include but are not limited to the structures below wherein the wavy lines indicate either ring bonds (as in the first of the above structures) or the points of attachment to R and the ring (as in the second of the above structures):

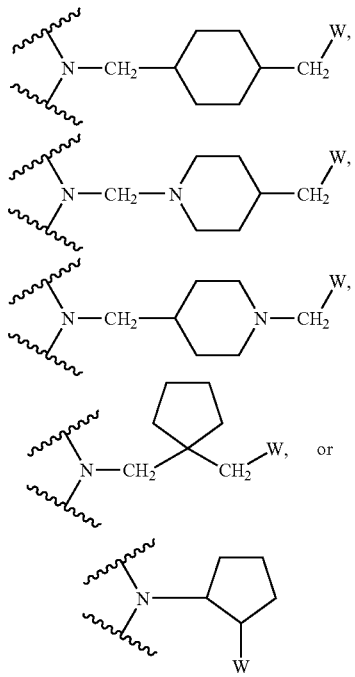

W is selected from acyl, hydroxyl, carboxyl, amino, carboxamido, sulfonamide, aminoacyl, —COOalkyl, —CHO, —C(O)fluoroalkyl, —C(O)CH$_2$C(O)Oalkyl, —C(O)CH$_2$C(O)Ofluoroalkyl, —SH, —C(O)NH(OH), —C(O)N(OH)R$^4$, —N(OH)C(O)OH, —N(OH)C(O)R$^4$, heterocyclyl, substituted aryl, and substituted heterocyclyl with R$^4$ being selected from the group consisting of H and lower alkyl.

In some embodiments, Ar is phenyl or substituted phenyl. These embodiments are illustrated by the formula:

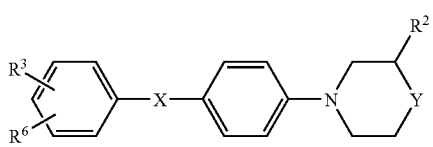

wherein R$^3$ and R$^6$ are independently selected from the group consisting of H, halogen, lower alkyl, fluoroloweralkyl, lower alkoxy, fluoroloweralkoxy, phenyl, and heteroaryl. In some embodiments R$^5$ is hydrogen; in others R$^5$ is —Z—W where Z is (CH$_2$)$_{1-4}$, and W is hydroxyl or carboxyl.

The present invention provides a method for inhibiting leukotriene A4 hydrolase comprising contacting the LTA4H enzyme with a therapeutically effective amount of a compound according to the general formula

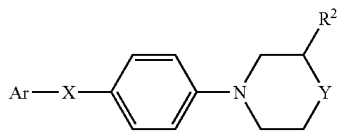

It may be found upon examination that additional species and genera not presently excluded are not patentable to the inventors in this application. In such a case, the exclusion of species and genera in applicants' claims are to be considered artifacts of patent prosecution and not reflective of the inventors' concept or description of their invention. The invention, in a composition aspect, is all compounds of the general formula above, except those that are in the public's possession. The invention, in a method aspect, is a method employing compounds of the general formula above, except those methods that are in the public's possession.

The present invention provides a method for treating a disorder associated with leukotriene A4 hydrolase comprising administering to a mammal a therapeutically effective amount of a compound or a salt, hydrate or ester thereof according to the general formula given above. In some embodiments the disorder is associated with inflammation. In some embodiments the disorder is selected from allergic inflammation, acute inflammation and chronic inflammation.

Compounds of the genus represented by the general formula above are inhibitors of $LTA_4H$ enzyme. As such they have utility in treating and preventing inflammatory diseases and disorders, as described above, particularly for such conditions as asthma, chronic obstructed pulmonary disease (COPD), atherosclerosis, rheumatoid arthritis, multiple sclerosis, inflammatory bowel diseases (IBD; including Crohn's disease and ulcerative colitis), or psoriasis, which are each characterized by excessive or prolonged inflammation at some stage of the disease.

Recent research indicates that the compounds are also useful for treating and preventing atherosclerosis, thrombosis, stroke, acute coronary syndrome, stable angina, peripheral vascular disease, critical leg ischemia, intermittent claudication, abdominal aortic aneurysm and myocardial infarction atherosclerosis, thrombosis, stroke, acute coronary syndrome and myocardial infarct.

The compounds may be presented as salts. The term "pharmaceutically acceptable salt" refers to salts whose counter ion derives from pharmaceutically acceptable non-toxic acids and bases. Suitable pharmaceutically acceptable base addition salts for the compounds of the present invention include, but are not limited to, metallic salts made from aluminum, calcium, lithium, magnesium, potassium, sodium and zinc or organic salts made from lysine, N,N-dialkyl amino acid derivatives (e.g. N,N-dimethylglycine, piperidine-1-acetic acid and morpholine-4-acetic acid), N,N'-dibenzylethylenediamine, chloroprocaine, choline, diethanolamine, ethylenediamine, meglumine (N-methylglucamine) and procaine. When the compounds contain a basic residue, suitable pharmaceutically acceptable base addition salts for the compounds of the present invention include inorganic acids and organic acids. Examples include acetate, benzenesulfonate (besylate), benzoate, bicarbonate, bisulfate, carbonate, camphorsulfonate, citrate, ethanesulfonate, fumarate, gluconate, glutamate, bromide, chloride, isethionate, lactate, maleate, malate, mandelate, methanesulfonate, mucate, nitrate, pamoate, pantothenate, phosphate, succinate, sulfate, tartrate, p-toluenesulfonate, and the like.

For convenience and clarity certain terms employed in the specification, examples and claims are described herein.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ hydrocarbon includes alkyl, cycloalkyl, alkenyl, alkynyl, aryl, arylalkyl and combinations thereof Examples include phenethyl, cyclohexylmethyl, camphoryl, adamantyl and naphthylethyl.

Alkoxy or alkoxyl refers to groups of from 1 to 8 carbon atoms of a straight, branched, cyclic configuration and combinations thereof attached to the parent structure through oxygen. Examples include methoxy, ethoxy, propoxy, isopropoxy, cyclopropyloxy, cyclohexyloxy and the like. Loweralkoxy refers to groups containing one to four carbons.

Alkoxyalkyl refers to ether groups of from 3 to 8 atoms of a straight, branched, cyclic configuration and combinations thereof attached to the parent structure through an alkyl. Examples include methoxymethyl, methoxyethyl, ethoxypropyl, and the like.

Alkoxyaryl refers to alkoxy substituents attached to an aryl, wherein the aryl is attached to the parent structure. Arylalkoxy refers to aryl substituents attached to an oxygen, wherein the oxygen is attached to the parent structure. Substituted arylalkoxy refers to a substituted aryl substituent attached to an oxygen, wherein the oxygen is attached to the parent structure.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or atricyclic 13- or 14-membered aromatic or heteroaromatic ring system containing 0-3 heteroatoms selected from O, N, or S. The aromatic 6- to 14-membered carbocyclic rings include, e.g., benzene and naphthalene, and according to the invention benzoxalane and residues in which one or more rings are aromatic, but not all need be. The 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. Examples include, e.g., pyridinylmethyl, pyrimidinylethyl and the like. Heterocyclylalkyl refers to a substituent in which a heterocyclyl residue is attached to the parent structure through alkyl. Examples include morpholinoethyl and pyrrolidinylmethyl.

Heterocycle means a cycloalkyl or aryl residue in which from one to three carbons is replaced by a heteroatom selected from the group consisting of N, O and S.

The nitrogen and sulfur heteroatoms may optionally be oxidized, and the nitrogen heteroatom may optionally be quaternized. Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

An oxygen heterocycle is a heterocycle containing at least one oxygen in the ring; it may contain additional oxygens, as well as other heteroatoms. A sulphur heterocycle is a heterocycle containing at least one sulphur in the ring; it may contain additional sulfurs, as well as other heteroatoms. A nitrogen heterocycle is a heterocycle containing at least one nitrogen in the ring; it may contain additional nitrogens, as well as other heteroatoms. Oxygen heteroaryl is a subset of oxygen heterocycle; examples include furan and oxazole. Sulphur heteroaryl is a subset of sulphur heterocycle; examples include thiophene and thiazine. Nitrogen heteroaryl is a subset of nitrogen heterocycle; examples include pyrrole, pyridine and pyrazine. A saturated nitrogenous heterocycle is a subset of nitrogen heterocycle. Saturated nitrogenous heterocycle contain at least one nitrogen and may contain additional nitrogens, as well as other heteroatoms. Examples include pyrrolidine, pyrazolidine, piperidine, morpholine, and thiomorpholine.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy, carboxy, carboalkoxy (also referred to as alkoxycarbonyl), carboxamide, cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The terms "halogen" and "halo" refer to fluorine, chlorine, bromine or iodine.

The term "prodrug" refers to a compound that is made more active in vivo. Activation in vivo may come about by chemical action or through the intermediacy of enzymes. Microflora in the GI tract may also contribute to activation in vivo.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^2H$, $^3H$, $^{13}C$, $^{14}C$, $^{15}N$, $^{35}S$, $^{18}F$, and $^{36}Cl$, respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Radiolabeled compounds of the present invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

As used herein, and as would be understood by the person of skill in the art, the recitation of "a compound" is intended to include salts, solvates, co-crystals and inclusion complexes of that compound.

The term "solvate" refers to a compound of formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Co-crystals are combinations of two or more distinct molecules arranged to create a unique crystal form whose physical properties are different from those of its pure constituents. Pharmaceutical co-crystals have recently become of considerable interest for improving the solubility, formulation and bioavailability of such drugs as itraconazole [see Remenar et al. J. Am. Chem. Soc. 125, 8456-8457 (2003)] and fluoxetine. Inclusion complexes are described in Remington: The Science and Practice of Pharmacy 19$^{th}$ Ed. (1995) volume 1, page 176-177. The most commonly employed inclusion complexes are those with cyclodextrins, and all cyclodextrin complexes, natural and synthetic, with or without added additives and polymer(s), as described in U.S. Pat. Nos. 5,324,718 and 5,472,954, are specifically encompassed within the claims. The disclosures of Remington and the '718 and '954 patents are incorporated herein by reference.

The compounds described herein may contain asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as, their racemic and optically pure forms. Optically active (R)- and (S)-isomers may be prepared using chiral synthons or chiral reagents, or resolved using conventional techniques. The prefix "rac" refers to a racemate. When the compounds described herein contain olefinic double bonds or other centers of geometric asymmetry, and unless specified otherwise, it is intended that the compounds include both E and Z geometric isomers. The representation of the configuration of any carbon-carbon double bond appearing herein is selected for convenience only, and unless explicitly stated, is not intended to designate a particular configuration. Thus a carbon-carbon double bond depicted arbitrarily as E may be Z, E, or a mixture of the two in any proportion. Likewise, all tautomeric forms are also intended to be included.

The graphic representations of racemic, ambiscalemic and scalemic or enantiomerically pure compounds used herein are taken from Maehr J. Chem. Ed. 62, 114-120 (1985): solid and broken wedges are used to denote the absolute configuration of a chiral element; wavy lines and single thin lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration.

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group, which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the Journal of Organic Chemistry. The list, which is typically presented in a table entitled "Standard List of Abbreviations", is incorporated herein by reference.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here. The starting materials, for example in the case of suitably substituted benzimidazole ring compounds, are either commercially available, synthesized as described in the examples or may be obtained by the methods well known to persons of skill in the art.

LTA4H inhibitors have been shown to be effective anti-inflammatory agents in pre-clinical studies. For example, oral administration of LTA4H inhibitor SC57461 to rodents resulted in the inhibition of ionophore-induced LTB4 production in mouse blood ex vivo, and in rat peritoneum in vivo (Kachur et al., 2002, J. Pharm. Exp. Ther. 300(2), 583-587). Furthermore, eight weeks of treatment with the same inhibitor compound significantly improved colitis symptoms in a primate model (Penning, 2001, Curr. Pharm. Des. 7(3): 163-179). The spontaneous colitis that develops in these animals is very similar to human IBD. Therefore persons of skill in the art accept that positive results in LTA4H models are predictive of therapeutic utility in this and other human inflammatory diseases.

The inflammatory response is characterized by pain, increased temperature, redness, swelling, or reduced function, or by a combination of two or more of these symptoms. The terms inflammation, inflammatory diseases or inflammation-mediated diseases or conditions include, but are not limited to, acute inflammation, allergic inflammation, and chronic inflammation.

Autoimmune diseases are associated with chronic inflammation. There are about 75 different autoimmune disorders known that may be classified into two types, organ-specific (directed mainly at one organ) and non-organ-specific (affecting multiple organs).

Examples of organ-specific autoimmune disorders are insulin-dependent diabetes (Type I) which affects the pancreas, Hashimoto's thyroiditis and Graves' disease which affect the thyroid gland, pernicious anemia which affects the stomach, Cushing's disease and Addison's disease which affect the adrenal glands, chronic active hepatitis which affects the liver; polycystic ovary syndrome (PCOS), celiac disease, psoriasis, inflammatory bowel disease (IBD) and ankylosing spondylitis.

Examples of non-organ-specific autoimmune disorders are rheumatoid arthritis, multiple sclerosis, systemic lupus and myasthenia gravis.

Furthermore, the compounds, compositions and methods of the present invention are useful in treating cancer. Leukotriene synthesis has been shown to be associated with different types of cancer including esophageal cancer, brain cancer, pancreatic cancer, colon cancer.

The terms "methods of treating or preventing" mean amelioration, prevention or relief from the symptoms and/or effects associated with lipid disorders. The term "preventing" as used herein refers to administering a medicament beforehand to forestall or obtund an acute episode. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis. Throughout this application, various references are referred to. The disclosures of these publications in their entireties are hereby incorporated by reference as if written herein.

The term "mammal" is used in its dictionary sense. Humans are included in the group of mammals, and humans would be the preferred subjects of the methods of.

While it may be possible for the compounds of the present invention to be administered as the raw chemical, it is preferable to present them as a pharmaceutical composition. According to a further aspect, the present invention provides a pharmaceutical composition comprising at least one compound described supra, or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association at least one compound of the present invention or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder (including micronized and nanoparticulate powders) or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Compositions of the present invention may also optionally include other therapeutic ingredients, anti-caking agents, preservatives, sweetening agents, colorants, flavors, desiccants, plasticizers, dyes, and the like. Any such optional ingredient must, of course, be compatible with the compound of the invention to insure the stability of the formulation. The dose range for adult humans is generally from 0.1 µg to 10 g/day orally. Tablets or other forms of presentation provided in discrete units may conveniently contain an amount of compound of the invention which is effective at such dosage or as a multiple of the same, for instance, units containing 0.1 mg to 500 mg, usually around 5 mg to 200 mg. The precise amount of compound administered to a patient will be the responsibility of the attendant physician. However, the dose employed will depend on a number of factors, including the age and sex of the patient, the precise disorder being treated, and its severity. The frequency of administration will depend on the pharmacodynamics of the individual compound and the formulation of the dosage form, which may be optimized by methods well known in the art (e.g. controlled or extended release tablets, enteric coating etc.).

Combination therapy can be achieved by administering two or more agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within any number of hours of each other or within any number or days or weeks of each other. In some cases even longer intervals are possible.

While in many cases it is desirable that the two or more agents used in a combination therapy be present in within the patient's body at the same time, this need not be so. Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y etc.

As LTA4H inhibitors, the compounds of formula Ψ have utility in treating and preventing inter alia inflammation. The compounds and compositions can be used advantageously in combination with other agents useful in treating and preventing inflammatory conditions and for treating and preventing atherosclerosis, thrombosis, stroke, acute coronary syndrome, stable angina, peripheral vascular disease, critical leg ischemia, intermittent claudication, abdominal aortic aneurysm and myocardial infarction.

In general, the compounds of the present invention may be prepared by the methods illustrated in the schemes as, for example, described below, or by modifications thereof, using readily available starting materials, reagents and conventional synthesis procedures. The following specific non-limiting examples are illustrative of the invenion.

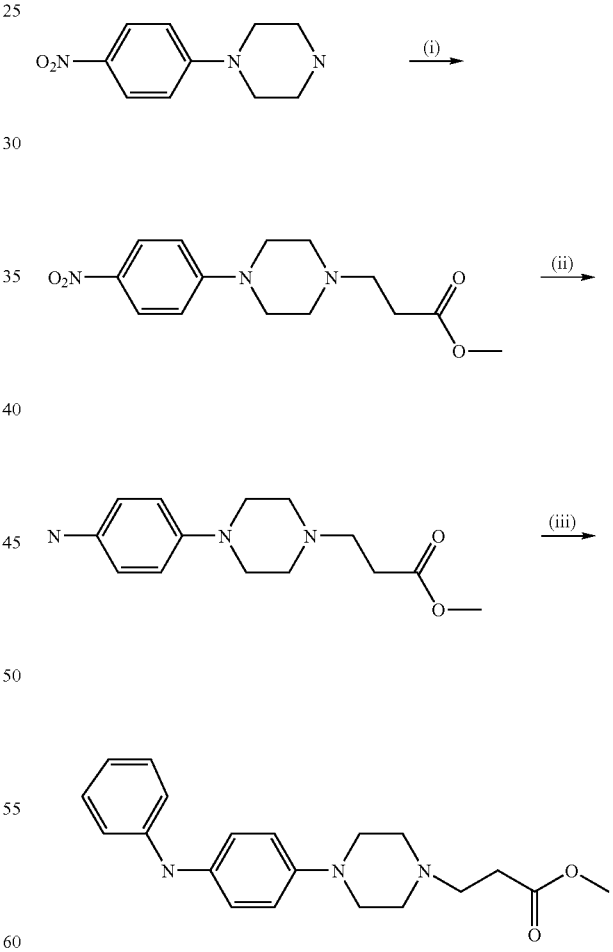

Scheme 1: (i) BrCH$_2$CH$_2$CO$_2$Me, DMF; (ii) H$_2$, Pd/C, EtOH; (iii) iodobenzene, Pd$_2$(dba)$_3$, Bu$_3$P

SCHEME II
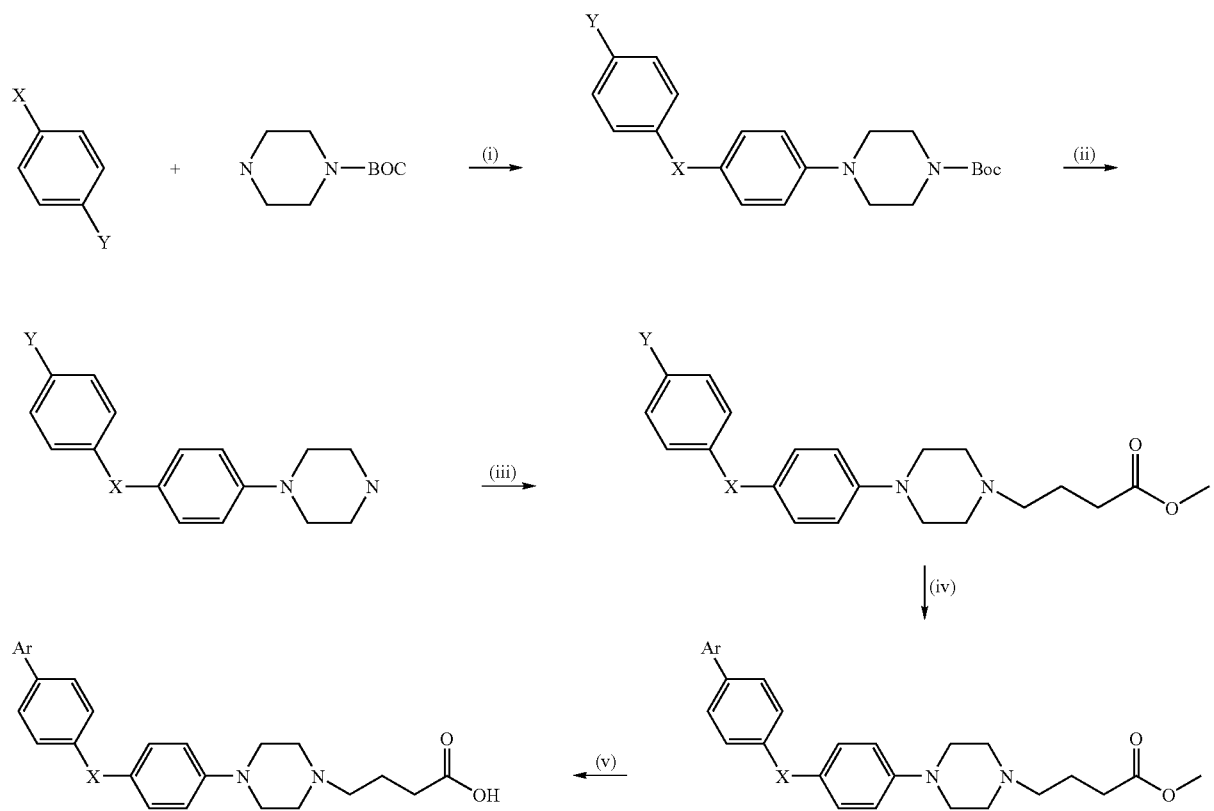
Scheme II: (i) Pd₂(dba)₃, Bu₃P; (ii) 4N HCl in dioxane; (iii) Br(CH₂)₂CO₂Me, DMF; (iv) ArX, Pd(OAc)₂, Ph₃P; (v) 1N NaOH
SCHEME III
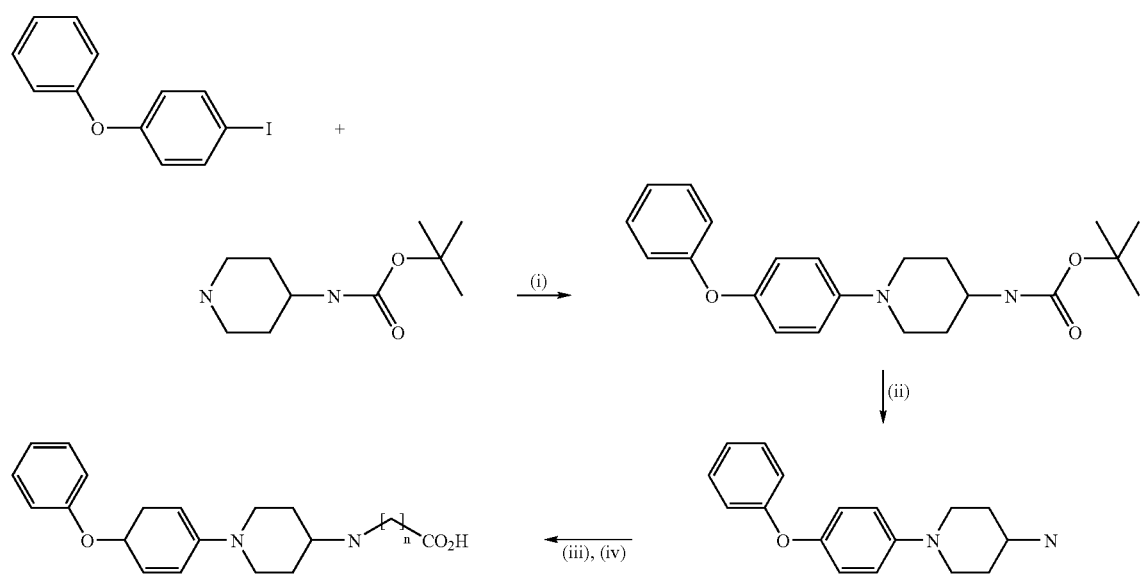
Scheme III: (i) Pd₂(dba)₃, DMF; (ii) 4N HCl in dioxane; (iii) Br(CH₂)nCO₂Me; (iv) 1N NaOH

SCHEME IV

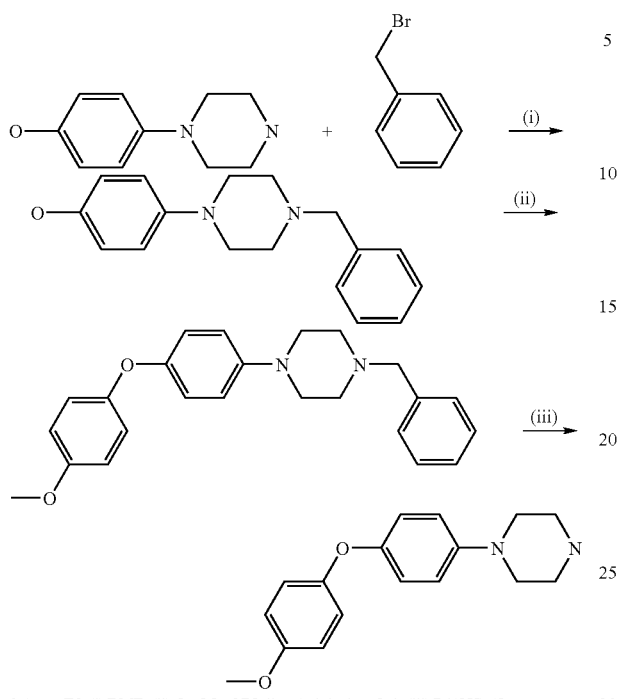

Scheme IV: (i) DMF; (ii) Cs₂CO₃, NN-dimethylglycine, CuI; (iii) Pd(OH)₂/C

EXAMPLES

Example 1

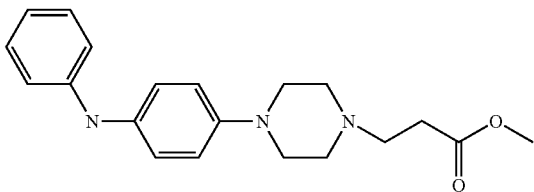

Step 1

3-[4-(4-Nitro-phenyl)-piperazin-1-yl]-propionic acid methyl ester: To a solution of 1-(4-nitro-phenyl)-piperazine (2 g, 9.66 mmol) in DMF (10 mL) was added 3-bromopropionic acid methyl ester (1.6 g, 9.66 mmol) and the mixture was stirred at ambient temperature for 16 h. Water was added to the reaction, followed by adjusting pH to 7 with sat. aqueous NaHCO₃. The resulting precipitate was collected by filtration and washed with water to furnish the title compound as a yellow solid (1.8 g, 63.6%): MS (ESI) m/z 294 (M+H); $^1$H NMR (400 MHz, CDCl₃) δ 2.55 (t, J=7.2 Hz, 2H), 2.62 (t, J=4.8 Hz, 4H), 2.77 (t, J=6.8 Hz, 2H), 3.42 (t, J=5.2 Hz, 4H), 3.71 (s, 3H), 6.81-6.83 (m, 2H), 8.11-8.14 (m, 2H).

Step 2

3-[4-(4-Amino-phenyl)-piperazin-1-yl]-propionic acid methyl ester: A mixture of the compound from step 1 (1.8 g), Pd/C (5%, 0.3 g) and ethanol (150 ml) was stirred at ambient temperature under hydrogen (1 atm) for 16 h. The reaction mixture was filtered and the solvent was removed under vacuum to furnish the title compound as a light tan solid (1.52 g, 94.6%): MS (ESI) m/z 264 (M+H); $^1$H NMR (400 MHz, CDCl₃) δ 2.55 (t, J=7.2 Hz, 2H), 2.65 (t, J=4.8 Hz, 4H), 2.77 (t, J=7.2 Hz, 2H), 3.05 (br, 4H), 3.70 (s, 3H), 6.80-6.83 (m, 2H), 8.11-8.14 (m, 2H).

Step 3

3-[4-(4-Phenylamino-phenyl)-piperazin-1-yl]-propionic acid methyl ester: The compound from step 2 (554 mg, 2.11 mmol) and iodobenzene (430 mg, 2.11 mmol) were dissolved in toluene (15 ml) and the following reagents were added: Pd₂(dba)₃ (58 mg, 0.063 mmol), P$^t$Bu3 (128 mg. 0.63 mmol) and NaO-t-Bu (202 mg, 2.11 mmol). The reaction mixture was stirred at ambient temperature overnight and then filtered. The filtrate was loaded onto a silica gel column and eluted with 1% MeOH in CH₂Cl₂ to yield the title compound as a yellow solid (85 mg, 11.9%): MS (ESI) m/z 340 (M+H); $^1$H NMR (400 MHz, CDCl₃) δ 2.56 (t, J=7.2 Hz, 2H), 2.64 (t, J=4.8 Hz, 4H), 2.77 (t, J=7.2 Hz, 2H), 3.13 (br, 4H), 3.69 (s, 3H), 6.82-7.21 (m, 9H).

Example 2

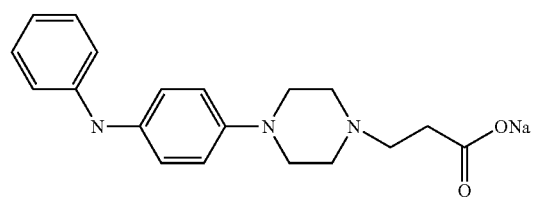

3-[4-(4-phenylamino-phenyl)-piperazin-1-yl]-propionic acid sodium salt: The compound from Example 1 (85 mg, 0.25 mmol) was dissolved in methanol (2 mL) followed by addition of 1N NaOH aqueous solution (0.27 ml, 0.27 mmol). The reaction solution was stirred at 60-70° C. for 4 h and then evaporated under vacuum to dryness. The residue was stirred with ethyl acetate (2 mL) and the solid was collected by filtration and washed with ethyl acetate to give the title product as an off-white solid (78 mg, 89.9%): MS (ESI) m/z 325 (M+1); $^1$H NMR (400 MHz, DMSO-d₆) δ 1.99 (m, 2H), 2.45-2.51 (m, 6H), 3.01 (t, J=4.8 Hz, 4H), 6.67 (m, 1H), 6.88 (m, 4H), 6.98 (d, J=9.2 Hz, 2H), 7.13 (m, 2H), 7.75 (s, 1H).

Example 3

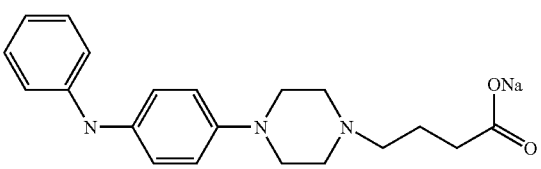

Step 1

4-[4-(4-Nitro-phenyl)-piperazin-1-yl]-butyric acid methyl ester: The title compound (1.56 g, 52.6%) was synthesized from 1-(4-nitro-phenyl)-piperazine (2 g, 9.66 mmol) and 4-bromo-butyric acid methyl ester (1.75 g, 9.83 mmol) by the procedure described in step 1 of Example 1 MS (ESI) m/z 264 (M+H); $^1$H NMR (400 MHz, CDCl₃) δ 1.86 (m, 2H), 2.39 (m, 4H), 2.58 (t, J=5.2 Hz, 4H), 3.41 (t, J=5.2, 4H), 3.68 (s, 3H), 6.81 (m, 2H), 8.12 (m, 2H).

Step 2

4-[4-(4-Amino-phenyl)-piperazin-1-yl]-butyric acid methyl ester: The title compound (1.2 g, 80%) was prepared from the compound from Step 1 (1.55 g, 5.78 mmol) by the procedure described in step 2 of Example 1 MS (ESI) m/z 293 (M+H); $^1$H NMR (400 MHz, CDCl$_3$) δ 1.85 (m, 2H), 2.39 (m, 4H), 2.58 (t, J=4.8 Hz, 4H), 3.04 (t, J=4.8, 4H), 3.67 (s, 3H), 6.64 (m, 2H), 6.80 (m, 2H) 1H).

Step 3

4-[4-(4-phenylamino-phenyl)-piperazin-1-yl]-butyric acid methyl ester: The title compound (120 mg, 34%) was prepared from the compound from step 2 (277 mg, 1 mmol) and iodobenzene (204 mg, 1 mmol) in the presence of Pd$_2$(dba)$_3$ (27 mg, 0.03 mmol), P$^t$Bu3 (60 mg. 0.3 mmol) and NaO-t-Bu (96 mg, 1 mmol) by the procedure described in step 3 of Example 1 MS (ESI) m/z 354 (M+H); $^1$H NMR (400 MHz, CDCl$_3$) δ 1.87 (m, 2H), 2.36-2.43 (m, 4H), 2.61 (b, 4H), 3.14 (b, 4H), 3.68 (s, 3H), 6.80-6.93 (m, 5H), 7.04 (d, J=8.8 Hz, 2H), 7.20 (t, J=8.0 Hz, 2H).

Step 4

4-[4-(4-phenylamino-phenyl)-piperazin-1-yl]-butyric acid sodium salt: The title compound (80 mg, 92.3%) was prepared from 4-[4-(4-phenylamino-phenyl)-piperazin-1-yl]-butyric acid methyl ester (86 mg, 0.24 mmol) and 1 N NaOH (0.25 mL, 0.25 mmol) by the procedure described in Example 2: MS (ESI) m/z 361 (M+1); $^1$H NMR (400 MHz, DMSO-d$_6$) δ 1.59 (m, 2H), 1.84 (t, J=7.2 Hz, 2H), 2.27 (t, J=7.6 Hz, 2H), 2.47 (t, J=4.8 Hz, 4H), 3.03 (t, J=4.8, 4H), 6.67 (m, 1H), 6.88 (m, 4H), 6.98 (d, J=9.2 Hz, 2H), 7.13 (m, 2H), 7.77 (s, 1H).

Example 4

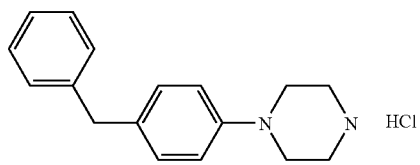

Step 1

4-(4-Benzyl-phenyl)-piperazine-1-carboxylic acid tert-butyl ester: To a solution of 1-Boc-piperazine (2.5 g, 13.1 mmol) and 4-iododiphenylmethane (4.0 g, 13.1 mmol) in toluene were added the following reagents: Pd$_2$(dba)$_3$ (0.36 g, 0.3 mmol), P$^t$Bu3 (0.7 g 3.0 mmol) and NaO-t-Bu (1.26 g, 13.1 mmol). The reaction mixture was stirred at ambient temperature overnight and then filtered. The filtrate was purified using silica gel chromatography (1% MeOH in CH$_2$Cl$_2$) to yield the title compound as a light tan oil (4.6 g, 99%): MS (ESI) m/z 353 (M+H); $^1$H NMR (400 MHz, CDCl$_3$) δ 1.47 (s, 9H), 3.08 (t, J=5.2 Hz, 4H), 3.56 (s, J=5.2 Hz, 4H), 3.91 (s, 2H), 6.85 (dd, J=2, 6.8 Hz, 2H), 7.09 (dd, J=2, 6.4 Hz, 2H), 7.16-7.19 (m, 3H), 7.25-7.29 (m, 2H).

Step 2

1-(4-Benzyl-phenyl)-piperazine hydrochloride: To 4-(4-Benzyl-phenyl)-piperazine-1-carboxylic acid tert-butyl ester (1.7 g, 4.8 mmol) was added 4 N HCl in dioxane (25 ml). The reaction solution was stirred at rt for 1 h. The resulting precipitate was collected by filtration and washed with ethyl acetate to furnish the title compound (1.45 g, 98%): MS (ESI) m/z 326 (M+1); $^1$H NMR (400 MHz, DMSO-d$_6$) δ 3.21 (br, 4H), 3.36 (br, 4H), 3.86 (s, 2H), 6.98 (m, 2H), 7.13-7.21 (m, 5H), 7.25-7.29 (m, 2H).

Example 5

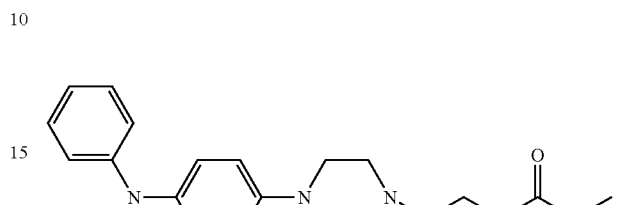

4-[4-(4-Benzyl-phenyl)-piperazin-1-yl]-butyric acid methyl ester: To a mixture of the compound from step 2 (500 mg, 1.5 mmol) and 4-bomobutyric acid methyl ester (278 mg, 1.5 mmol) in DMF (5 mL) was added triethylamine (454 mg, 1.53 mmol) dropwise and the reaction mixture was stirred at ambient temperature overnight. The mixture was poured onto water and extracted with ethyl acetate (50 ml×3). The combined organic layers were washed with brine, dried over anhy. Na$_2$SO$_4$ and evaporated under vacuum to dryness. The residue was purified by silica gel flash chromatography (1% methanol in CH$_2$Cl$_2$) to furnish the title compound (430 mg, 81.4%): MS (ESI) m/z 353 (M+1); $^1$H NMR (400 MHz, CDCl$_3$) δ 1.85 (m, 2H), 2.36-2.43 (m, 4H), 2.58 (t, J=4.8, 4H), 3.15 (t, J=4.8 Hz, 4H), 3.67 (s, 3H), 3.90 (s, 2H), 6.85 (dd, J=2.0, 6.4 Hz, 2H), 7.06-7.08 (d, J=9.2 Hz, 2H), 7.16-7.19 (m, 3H), 7.25-7.29 (m, 2H).

Example 6

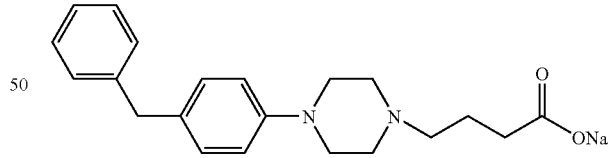

4-[4-(4-Benzyl-phenyl)-piperazin-1-yl]-butyric acid sodium salt: The title compound (380 mg, 90.9%) was prepared from the compound from Example 4 (410 mg, 1.16 mmol) and 1N NaOH (1.27 mL, 1.27 mmol) by the procedure described in Example 2 MS (ESI) m/z 360 (M+Na); $^1$H NMR (400 MHz, DMSO-d$_6$) δ 1.57 (m, 2H), 1.81 (t, J=7.6 Hz, 2H), 2.24 (t, J=7.6 Hz, 2H), 2.44 (t, J=4.8 Hz, 4H), 3.05 (t, J=4.8 Hz, 4H), 3.81 (s, 2H), 6.83 (d, J=8.8 Hz, 2H), 7.04 (d, J=8.2 Hz, 2H), 7.15-7.28 (m, 5H). Anal. Calcd for C21H26N2O2Na.2H2O: C, 63.46; H, 7.61; N, 7.05. Found: C, 63.08; H, 7.00; N, 7.06.

Example 7

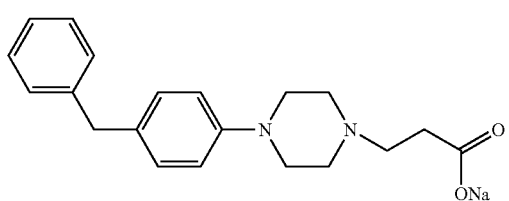

Step 1

3-[4-(4-Benzyl-phenyl)-piperazin-1-yl]-propionic acid sodium salt: 3-[4-(4-Benzyl-phenyl)-piperazin-1-yl]-propionic acid methyl ester (120 mg, 42.6%) was prepared from 1-(4-Benzyl-phenyl)-piperazine hydrochloride (250 mg, 0.77 mmol) and 3-bromo-propionic acid methyl ester (128 mg, 0.77 mmol) using the method described in Example 5. Following the procedure described in Example 2, the ester (120 mg, 0.35 mmol) was treated with 1N NaOH (0.43 mL, 0.43 mmol) to yield the title compound (110 mg, 89.5%): MS (ESI) m/z 325 (M+1); $^1$H NMR (400 MHz, DMSO-$d_6$) δ 2.02 (t, J=7.6 Hz, 2H), 2.43-2.51 (m, 6H), 3.03 (t, J=4.8 Hz, 4H), 3.81 (s, 2H), 6.83 (d, J=8.8 Hz, 2H), 7.04 (d, J=8.8 Hz, 2H), 7.14-7.19 (m, 3H), 7.26 (m, 2H).

Example 8

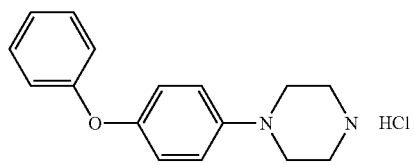

Step 1

4-(4-Phenoxy-phenyl)-piperazine-1-carboxylic acid tert-butyl ester: The title compound (3.5 g, 75.5%) was prepared from 1-iodo-4-phenoxy-benzene (3.9 g, 13.1 mmol) and 1-Boc-piperazine (2.5 g, 13.1 mmol) by the procedure described in step 1 of Example 4: MS (ESI) m/z 355 (M+H); $^1$H NMR (400 MHz, CDCl$_3$) δ 1.49 (s, 9H), 3.08 (t, J=4.8 Hz, 4H), 3.59 (t, J=4.8 Hz, 4H), 6.90-7.09 (m, 7H), 7.27-7.32 (m, 2H).

Step 2

1-(4-Phenoxy-phenyl)-piperazine hydrochloride: The title compound (2.8 g, 99%) was prepared from the compound from step 1 (3.0 g, 8.45 mmol) and 4N HCl in dioxane using the procedure described in step 2 of Example 4: MS (ESI) m/z 255 (M+H); $^1$H NMR (400 MHz, DMSO-$d_6$) δ 3.22 (br, 4H), 3.34 (t, J=4.8 Hz, 4H), 6.91-6.98 (m, 4H), 7.03-7.09 (m, 3H), 7.34 (m, 2H), 9.23 (br, 2H). Anal. Calcd for C16H18N2O.2HCl.0.8H2O: C, 58.72; H, 6.16; N, 8.56. Found: C, 56.25; H, 6.37; N, 8.20.

Example 9

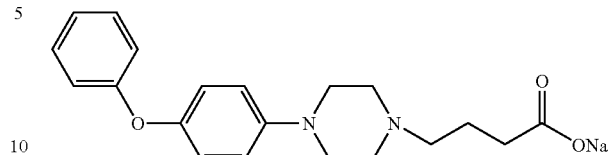

Step 1

4-[4-(4-Phenoxy-phenyl)-piperazin-1-yl]-butyric acid methyl ester: The title compound (106 mg, 32.6%) was prepared from the compound from step 2, Example 8 (165 mg, 0.9 mmol) and 4-bromo-butyric acid methyl ester (165 mg, 90 mmol) by the procedure described in step 3 of Example 4: MS (ESI) m/z 355 (M+H); $^1$H NMR (400 MHz, CDCl$_3$) δ 1.84 (m, 2H), 2.36-2.44 (m, 4H), 2.60 (t, J=4.8 Hz, 4H), 3.14 (t, J=4.8 Hz, 4H), 3.68 (s, 3H), 6.89-7.04 (m, 7H), 7.26-7.29 (m, 1H).

Step 2

4-[4-(4-Phenoxy-phenyl)-piperazin-1-yl]-butyric acid sodium salt: The title compound (75 mg. 69%) was prepared from the compound from step 3 (106 mg, 2.98 mmol) and 1N NaOH (0.3 mL, 0.3 mmol) by the procedure described in Example 2: MS (ESI) m/z 341 (M+Na); $^1$H NMR (400 MHz, DMSO-$d_6$) δ 1.59 (m, 2H), 1.82 (t, J=7.2 Hz, 2H), 2.26 (t, J=8 Hz, 2H), 2.47 (t, J=5.2 Hz, 4H), 3.08 (t, J=4.6 Hz, 4H), 6.89-6.97 (m, 6H), 7.04 (m, 1H), 7.32 (m, 2H).

Example 10

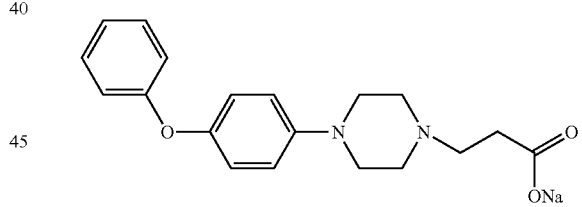

Step 1

3-[4-(4-Phenoxy-phenyl)-piperazin-1-yl]-propionic acid methyl ester: The title compound (126 mg, 40.4%) was prepared from 1-(4-Phenoxy-phenyl)-piperazine hydrochloride (165 mg, 0.9 mmol) and 3-bromo-propionic acid methyl ester (158 mg, 0.94 mmol) by the procedure described in step 3 of Example 4: MS (ESI) m/z 341 (M+H); $^1$H NMR (400 MHz, CD$_3$OD) δ 2.55 (m, 2H), 2.64 (b, 4H), 2.76 (m, 2H), 3.15 (b, 4H), 3.70 (s, 2H), 6.88-7.05 (m, 7H), 7.28 (m, 2H).

Step 2

3-[4-(4-Phenoxy-phenyl)-piperazin-1-yl]-propionic acid sodium salt: The title compound (98 mg, 97%) was prepared from the compound from step 1 (100 mg, 0.29 mmol) and 1N NaOH (0.29 mL, 0.29 mmol) by the procedure described in Example 2: MS (ESI) m/z 327 (M+H); $^1$H NMR (400 MHz, CD$_3$OD) δ 2.44 (m, 2H), 2.72 (t, J=4.8 Hz, 4H), 2.78 (t, J=8.0 Hz, 2H), 3.17 (t, J=4.8 Hz, 4H), 6.88-6.92 (m, 4H), 6.97-7.04 (m, 3H), 7.28 (m, 2H).

Example 11

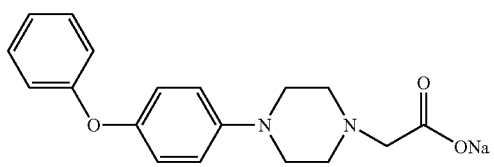

Step 1

2-[4-(4-Phenoxy-phenyl)-piperazin-1-yl]-acetic acid methyl ester: The title compound (135 mg, 41%) was prepared from 1-(4-Phenoxy-phenyl)-piperazine hydrochloride. (165 mg, 0.9 mmol) and methyl 2-bromo-acetate (140 mg, 0.92 mmol) by the procedure described in step 3 of Example 6 MS (ESI) m/z 327 (M+H); $^1$H NMR (400 MHz, CDCl$_3$) δ 2.76 (b, 2.67), 3.21 (t, J=3.2 Hz, 4H), 3.29 (s, 2H), 3.75 (s, 3H), 6.92-7.05 (m, 7H), 7.29 (m, 2H).

Step 2

2-[4-(4-Phenoxy-phenyl)-piperazin-1-yl]-acetic acid sodium salt. The title compound (96 mg, 95%) was prepared from the compound from step 1 (100 mg, 0.30 mmol) and 1N NaOH (0.3 mL, 0.3 mmol) by the procedure described in Example 2: MS (ESI) m/z 313 (M+H); $^1$H NMR (400 MHz, DMSO-d$_6$) δ 2.57 (t, J=4.8 Hz, 4H), 2.67 (s, 2H), 3.07 (t, J=4.8 Hz, 4H), 6.89-6.96 (m, 6H), 7.04 (m, 1H), 7.32 (m, 2H).

Example 12

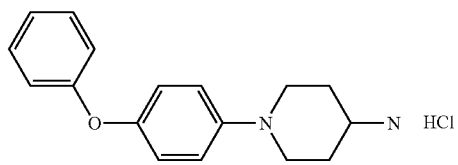

Step 1

[1-(4-Phenoxy-phenyl)-piperidin-4-yl]-carbamic acid tert-butyl ester: The title compound (1.1 g, 30%) was prepared from 1-iodo-4-phenoxy-benzene (2.9 g, 10 mmol) and piperidin-4-yl-carbamic acid tert-butyl ester (2 g, 10 mmol) by the procedure described in step 1 of Example 4: MS (ESI) m/z 368 (M+H); $^1$H NMR (400 MHz, CDCl$_3$) δ 1.46 (s, 9H), 1.51-1.61 (m, 3H), 2.05 (br, 2H), 2.81 (dd, J=1.6, 12 Hz, 2H), 3.52 (m, 2H), 3.60 (br, 1H), 4.47 (br, 1H), 6.90-6.96 (m, 6H), 7.03 (m, 1H), 7.28 (m, 2).

Step 2

1-(4-Phenoxy-phenyl)-piperidin-4-ylamine hydrochloride: The title compound (0.21 g, 76%) was prepared from the compound from step 1 (0.30 g, 0.81 mmol) and 4 N HCl in dioxane by the procedure described in step 2 of Example 4: MS (ESI) m/z 269 (M+H); $^1$H NMR (500 MHz, DMSO-d$_6$) δ 1.86 (br, 2H), 2.08 (m, 2H), 3.10 (br, 1H), 3.30 (br, 2H) 3.66 (m, 2H), 5.25 (br, 2H), 6.96-7.03 (m, 4H), 7.12 (m, 2H). 7.38 (m, 3H), 8.22 (br, 2H).

Example 13

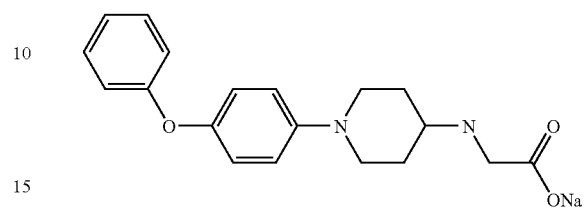

Step 1

[1-(4-Phenoxy-phenyl)-piperidin-4-ylamino]-acetic acid methyl ester: The title compound (24 mg, 21%) was prepared from the compound from Example 12 (120 mg, 0.35 mmol) and 2-bromoacetic acid methyl ester (53 mg, 0.35 mmol) by the procedure described in step 1 of Example 1: MS (ESI) m/z 341 (M+H); $^1$H NMR (400 MHz, CDCl$_3$) δ 1.51-1.61 (m, 4H), 1.95 (br, 2H), 2.61 (m, 11H), 2.75 (dd, J=2.4, 12 Hz, 2H), 3.56 (m, 2H), 3.75 (s, 3H), 6.90-6.96 (m, 6H), 7.03 (m, 1H), 7.28 (m, 2).

Step 2

[1-(4-Phenoxy-phenyl)-piperidin-4-ylamino]-acetic acid sodium salt: The title compound (23 mg, 94%) was prepared from the compound from step 1 (24 mg, 0.07 mmol) and 1N NaOH (0.07 mL. 0.07 mmol) by the procedure described in Example 2: MS (ESI) m/z 327 (M+H); $^1$H NMR (400 MHz, DMSO-d$_6$) δ 1.36 (m, 2H), 1.80 (m, 2H), 2.45-2.55 (m, 2H), 2.68 (dd, J=2.8, 12 Hz, 2H), 3.53 (m, 2H), 6.88-6.91 (m, 4H), 6.95 (m, 2H), 7.04 (m, 1H), 7.32 (m, 2H).

Example 14

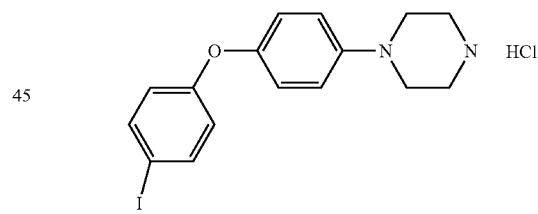

Step 1

4-[4-(4-Iodo-phenoxy)-phenyl]-piperazine-1-carboxilic acid tert-butyl ester: The title compound (0.25 g, 20.8%) was prepared from 4,4-diiododipheyl ether (1.07 g, 2.5 mmol) and 1-Boc-piperazine (0.47 g, 2.5 mmol) in the presence of Pd$_2$(dba)$_3$ (0.07 g, 0.075 mmol), P$^t$Bu3 (0.15 g. 2.5 mmol) and NaO-t-Bu (0.24 g, 2.5 mmol) by the procedure described in step 1 of Example 4. MS (ESI) m/z 481 (M+H); $^1$H NMR (400 MHz, CDCl$_3$) δ 1.49 (s, 9H), 3.08 (t, J=4.8 Hz, 4H), 3.59 (t, J=4.8 Hz, 4H), 6.71 (m, 2H), 6.90-6.97 (m, 4H), 7.56 (m, 2H).

Step 2

1-[4-(4-Iodo-phenoxy)-phenyl]-piperazine hydrochloride: The title compound (1.3 g, 95%) was prepared from the compound from step 1 (1.35 g, 3.8 mmol) and 4N HCl in dioxane by the procedure described in step 2 of Example 4: MS (ESI) m/z 381 (M+H); $^1$H NMR (400 MHz, DMSO-d$_6$) δ

3.22 (br, 4H), 3.32 (t, J=5.6 Hz, 4H), 6.74 (d, J=8.8 Hz, 2H), 6.98-7.03 (m, 4H), 7.65 (d, J=8.8 Hz, 2H), 9.05 (br, 1H).

Example 15

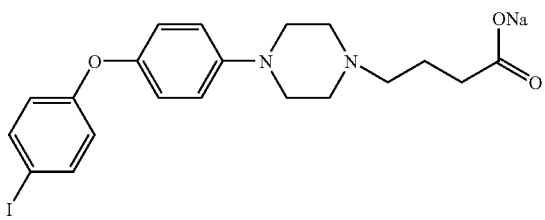

Step 1

4-{4-[4-(4-Iodo-phenoxy)-phenyl]-piperazin-1-yl]-butyric acid methyl ester: The title compound (300 mg, 85%) was prepared from the compound from step 2 of Example 14 (300 mg, 0.66 mmol) and 4-bromo-butyric acid methyl ester (153 mg, 0.85 mmol) by the procedure described in step 3 of Example 4: MS (ESI) m/z 481 (M+H); $^1$H NMR (400 MHz, CDCl$_3$) δ 1.86 (m, 2H), 2.36-2.44 (m, 4H), 2.60 (t, J=4.8 Hz, 4H), 3.15 (t, J=4.8 Hz, 4H), 3.68 (s, 3H), 6.70 (s, J=8.8 Hz, 2H), 6.92 (m, 4H), 7.55 (d, J=8.8 Hz, 2H).

Step 2

4-{4-[4-(4-Iodo-phenoxy)-phenyl]-piperazin-1-yl]-butyric acid sodium salt: The title compound (15 mg. 38%) was prepared from the compound from step 1 (39 mg, 0.081 mmol) and 1N NaOH (0.11 mL, 0.11 mmol) by the procedure described in Example 2: MS (ESI) m/z 467 (M+1); $^1$H NMR (400 MHz, DMSO-d$_6$) δ 1.59 (m, 2H), 1.83 (t, J=7.2 Hz, 2H), 2.27 (t, J=7.6 Hz, 2H), 2.47 (t, J=4.8 Hz, 4H), 3.09 (t, J=4.8 Hz, 4H), 6.74 (dd, J=2.0, 6.8 Hz, 2H), 6.91-6.98 (m, 4H), 7.63 (dd, J=2.4, 6.4 Hz, 2H).

Example 16

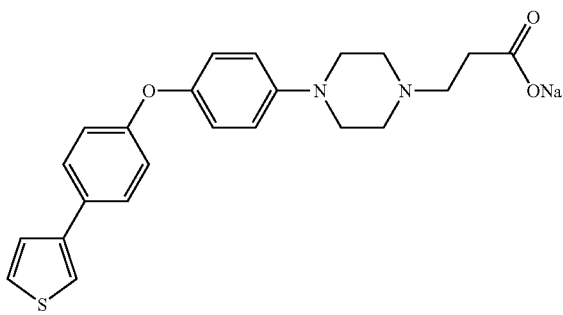

Step 1

3-{4[4-(4-Iodo-phenoxy)-phenyl]-piperazin-1-yl}-propionic acid methyl ester: The title compound (280 mg, 91%) was prepared from the compound from Example 14 (300 mg, 0.66 mmol) and 3-bromo-propionic acid methyl ester (153 mg, 0.92 mmol) by the procedure described step 1 of Example 1 MS (ESI) m/z 467 (M+H); $^1$H NMR (400 MHz, CDCl$_3$) δ 2.56 (t, J=7.2 Hz, 2H), 2.64 (t, J=4.8 Hz, 4H), 2.75 (t, J=7.2 Hz, 2H), 3.15 (t, J=4.8 Hz, 4H), 3.69 (s, 3H), 6.70 (dd, J=0.8, 8.8 Hz, 2H), 6.92 (m, 4H), 7.56 (dd, J=0.8, 8.4 Hz, 2H).

Step 2

3-{4[4-(4-Thiophen-3-yl-phenoxy)-phenyl]-piperazin-1-yl}-propionic acid methyl ester: To a mixture of the compound from step 1 (140 mg, 0.3 mmol), thiophene-3-boronic acid (70 mg, 055 mmol), palladium(II) acetate (20 mg, 0.09 mmol) and triphenyl phosphine (40 mg, 0.18 mmol) in DME (5 mL) was added potassium carbonate (140 mg, 1 mmol), ethanol (0.5 mL) and water (0.5 mL). The mixture was stir at rt under Ar for 30 min and then was heated to 80° C. for 16 h. After cooling to rt temperature, the mixture was poured onto 20 mL ice-water, followed by extraction with EtOAc (3×10 mL). The combined organic layers were washed with water (2×10 mL), brine (10 mL) and dried over anhydrous Na$_2$SO$_4$. The solvent was removed under reduced pressure to obtain the crude product, which was purified by silica gel flash chromatography (1% MeOH in CH$_2$Cl$_2$) to afford the title product (45 mg, 35%): MS (ESI) m/z 423 (M+H); $^1$H NMR (400 MHz, CDCl$_3$) δ 2.56 (t, J=7.2 Hz, 2H), 2.64 (t, J=4.8 Hz, 4H), 2.77 (t, J=7.2 Hz, 2H), 3.16 (t, J=4.8 Hz, 4H), 3.70 (s, 3H), 6.90-6.99 (m, 6H), 7.34-7.37 (m, 3H), 7.51 (m, 2H).

Step 3

3-{4[4-(4-Thiophen-3-yl-phenoxy)-phenyl]-piperazin-1-yl}-propionic acid sodium salt: The title compound (13 mg, 86%) was prepared from the compound from step 2 (15 mg, 0.035 mmol) and 1N NaOH (0.036 mL, 0.036 mmol) by the procedure described in Example 2: MS (ESI) m/z 409 (M+H). $^1$H NMR (400 MHz, CD$_3$OD) δ 2.44 (m, 2H), 2.70 (t, J=4.8 Hz, 4H), 2.76 (m, 2H), 3.17 (t, J=4.8 Hz, 4H), 6.91-6.96 (m, 4H), 7.02 (m, 2H), 7.39 (dd, J=1.6, 4.8 Hz, 1H), 7.44 (m, 1H), 7.51 (dd, J=1.2, 2.8 Hz, 1H), 7.58 (m, 2H).

Example 17

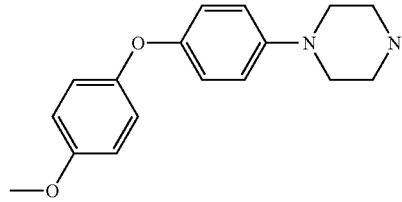

Step 1

4-(4-Benzyl-piperazin-1-yl)-phenol: To a solution of 4-piperazin-1-yl-phenol (1.78 g, 10 mmol) in DMF (20 mL) was added bromomethyl-benzene (1.71 g, 10 mmol) dropwise and then the reaction was stirred at room temperature for 16 h. The mixture was poured into water and pH was adjusted to 7 with sat. aqueous NaHCO$_3$, and then extracted with ethyl acetate (100 ml×2). The combined organic layers were washed with water and dried over anhy. Na$_2$SO$_4$. After removing the solvent under vacuum, the title compound was obtained (1.1 g, 41%) and MS (ESI) m/z 269 (M+H). $^1$H NMR (400 MHz, CDCl$_3$) δ 2.62 (t, J=4.8 Hz, 4H), 3.08 (t, J=4.8 Hz, 4H), 3.57 (s, 2H), 6.74 (d, J=8.8 Hz, 2H), 6.83 (d, J=8.8 Hz, 2H), 7.28-7.34 (m, 5H).

Step 2

1-Benzyl-4-[4-(4-methoxy-phenoxy)-phenyl]-piperazine: To a solution of the compound from step 1 (0.59 g, 2 mmol) and 1-iodo-4-methoxy-benzene (0.47 g, 2 mmol) in anhydrous dioxane (8 mL) were added cesium carbonate (1.26 g, 4 mmol), N,N-dimethylglycine. HCl (0.036 g, 0.25 mmol), and copper (I) iodide (0.015 g, 0.078 mmol) and the reaction mixture was stirred at 90° C. for 24 h under nitrogen. The mixture was filtered and partitioned between ethyl acetate (153 mL) and water (100 mL). The organic layers were washed with brine, dried over anhydrous Na$_2$SO$_4$, and concentrated to give a off-white oil, which was purified by silica gel flash chromatography to afford the title product (85 mg, 11.4%) as a light yellow solid: MS (ESI) m/z 359 (M+H). $^1$H NMR (400 MHz, CDCl$_3$) δ 2.62 (t, J=4.8 Hz, 4H), 3.14 (t, J=4.8 Hz, 4H), 3.57 (s, 2H), 3.78 (s, 3H), 6.83-6.93 (m, 8H), 7.30-7.34 (m, 5H).

Step 3

1-[4-(4-Methoxy-phenoxy)-phenyl]-piperazine: A mixture of the compound from step 2 (52 mg, 0.13 mmol), Pd(OH)$_2$/C (20%, 5 mg) and methanol (3 mL) was stirred at ambient temperature under hydrogen (1 atm) for 24 h. The reaction mixture was filtered and the solvent was removed under vacuum to furnish the title compound (29 mg, 78.5%) as an off-white oil: MS (ESI) m/z 285 (M+H); $^1$H NMR (400 MHz, CDCl$_3$) δ 2.31 (s, 3H), 3.12 (m, 4H), 3.16 (m, 4H), 6.85 (d, J=8.4 Hz, 2H), 6.89-6.95 (m, 4H), 7.11 (dd, J=0.8, 8.0 Hz, 2H).

Example 18

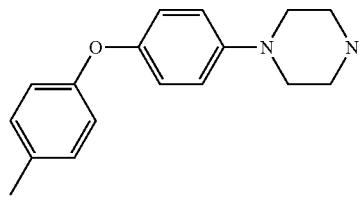

Step 1

1-Benzyl-4-(4-p-tolyloxy-phenyl]-piperazine: The title compound (103 mg, 14.3%) was prepared from 4-(4-benzyl-piperazin-1-yl)-phenol (530 mg, 2 mmol) and 1-iodo-4-methyl-benzene (430 mg, 2 mmol) by the procedures described in step 2 of Example 17: MS (ESI) m/z 359 (M+H); $^1$H NMR (400 MHz, CDCl$_3$) δ 2.30 (s, 3H), 2.62 (t, J=4.8 Hz, 4H), 3.15 (t, J=4.8 Hz, 4H), 3.57 (s, 2H), 6.84-6.94 (m, 6H), 7.08 (dd, J=0.6, 8.4 Hz, 2H), 7.31-7.35 (m, 5H).

Step 2

1-(4-p-Tolyloxy-phenyl]-piperazine: The title compound (28 mg, 72%) was prepared from the compound from step 1 (53 mg, 0.15 mmol) by the procedure described in step 3 of Example 17: MS (ESI) m/z 269 (M+H); $^1$H NMR (400 MHz, CDCl$_3$) δ 3.08 (m, 4H), 3.15 (m, 4H), 3.49 (s, 3H), 6.85 (d, J=8.8 Hz, 2H), 6.88-6.95 (m, 4H), 7.09 (d, J=8.8 Hz, 2H).

Example 19

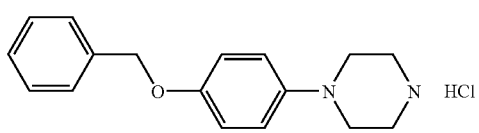

Step 1

4-(4-Benzyloxy-phenyl)-piperazin-1-carboxylic acid tert-butyl ester: A mixture of 4-(4-hydroxy-phenyl)-piperazin-1-carboxylic acid tert-butyl ester (278 mg, 1 mmol), bromomethyl-benzene (171 mg, 1 mmol) and K$_2$CO$_3$ (138 mg, 1 mmol) in DMF (3 mL) was stirred at rt for 24 h and then at 50° C. for 6 h, followed by addition of water (150 mL). The resulting solid was collected by filtration and washed with water to yield the desired compound (340 mg, 92%) as a white solid: MS (ESI) m/z 369 (M+H); $^1$H NMR (400 MHz, CDCl$_3$) δ 1.48 (s, 9H), 3.01 (t, J=4.8 Hz, 4H), 3.57 (t, J=4.8 Hz, 4H), 5.02 (s, 2H), 6.87-6.93 (m, 4H), 7.33-7.44 (m, 5H).

Step 2

1-(4-Benzyloxy-phenyl]-piperazine hydrochloride: The title compound (260 mg, 89.1%) was prepared from the compound from step 1 (300 mg, 0.82 mmol) and 4N HCl in dioxane by the procedure described in step 1 of Example 4: MS (ESI) m/z 269 (M+H); $^1$H NMR (500 MHz, DMSO-d$_6$) δ 3.22 (br, 8H), 5.04 (s, 2H). 6.94 (br, 4H), 7.30-7.43 (m, 5H), 9.00 (br, 2H).

Example 20

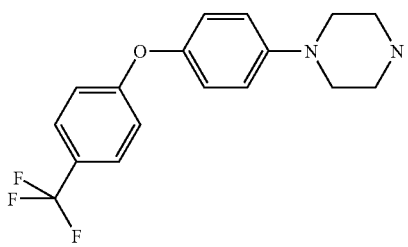

Step 1

1-Benzyl-4-[4-(4-trifluoromethyl-phenoxy)-phenyl]-piperazine: The title compound (120 mg, 25%) was prepared from 4-(4-benzyl-piperazin-1-yl)-phenol (268 mg, 1 mmol) and 1-iodo-4-trifluoromethyl-benzene (270 mg, 1 mmol) by the procedure described in step 2 of Example 17: MS (ESI) m/z 413 (M+H): $^1$H NMR (400 MHz, CDCl$_3$) δ 2.63 (br, 4H), 3 18 (br, 4H), 3.58 (s, 2H), 6.92-6.98 (m, 6H), 7.32-7.35 (m, 5H), 7.52 (d, J=7.2 Hz, 2H).

Step 2

1-[4-(4-Trifluoromethyl-phenoxy)-phenyl]-piperazine: The title compound (66 mg, 70%) was prepared from the compound from step 1 (120 mg, 0.29 mmol) by the procedure described in step 3 of Example 17: MS (ESI) m/z 323 (M+H); $^1$H NMR (400 MHz, CDCl$_3$) δ 3.10 (m, 4H), 3.21 (m, 4H), 6.94-7.01 (m, 6H), 7.53 (d, J=8.8 Hz, 2H).

Example 21

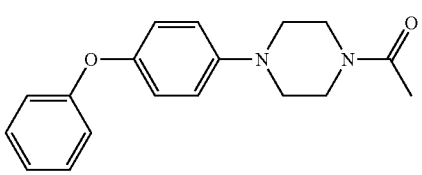

1-[4-(4-Phenoxy-phenyl)-piperazin-1-yl]-ethanone: To a solution of the compound from Example 8, step 2 (100 mg 0.3 mmol) in CH$_2$Cl$_2$ was added acetic anhydride (0.1 mL) and triethylamine (0.4 mL) sequentially at rt. The reaction mixture was stirred at it for 1 h and poured onto water (100 mL). The precipitate was collected by filtration and washed with water to give the title compound (58 mg, 64%) as an off-white solid: MS (ESI) m/z 297 (M+H); $^1$H NMR (400 MHz, CDCl$_3$) δ 2.15 (s, 3H), 3.12 (m, 4H), 3.63 (t, J=5.2 Hz, 2H), 3.78 (t, J=5.2 Hz, 2H), 6.91-6.99 (m, 6H), 7.05 (m, 1H), 7.28-7.32 (m, 2H).

Example 22

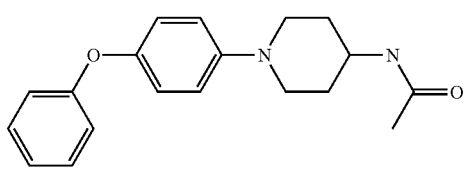

N-[1-(4-Phenoxy-phenyl)-piperidin-4-yl]-acetamide: The title compound (75 mg, 80%) was prepared from the compound from Example 12, step 2 (100 mg, 0.3 mmol) and acetic anhydride by the procedure described in Example 14: MS (ESI) m/z 311 (M+H); $^1$H NMR (400 MHz, CDCl$_3$) δ 1.58 (m, 2H), 2.08 (m, 2H), 2.84 (dd, J=2.8, 12 Hz, 2H), 3.54 (dd, J=2.8, 12.8 Hz, 2H), 3.93 (m, 1H), 5.35 (d, J=7.2 Hz, 1H), 6.91-6.97 (m, 6H), 7.03 (m, 1H), 7.27-7.31 (m, 2H).

Example 23

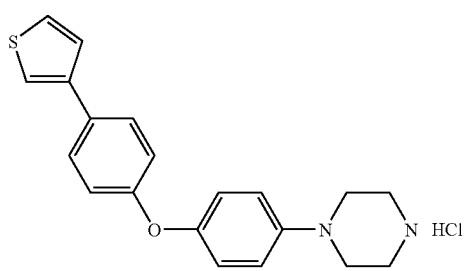

Step 1

1-[4-(4-Thiophen-3yl-phenoxy)-phenyl]-piperazine-1-carboxyli acid tert-butyl ester: The title compound (0.1 g, 76%) was synthesized from 4-[4-(4-Iodo-phenoxy)-phenyl]-piperazine-1-carboxilic acid tert-butyl ester (0.14 g, 2.1 mmol; from step 1 of Example 14), thiophene-3-boronic acid (70 mg, 055 mmol), palladium(II) acetate (20 mg, 0.09 mmol) and triphenyl phosphine (40 mg, 0.18 mmol), potassium carbonate (140 mg, 1 mmol), in DME (5 mL) in the presence of ethanol (0.5 mL) and water (0.5 mL) by using the procedure described in step 2 of Example 16: MS (ESI) m/z 437 (M+H); $^1$H NMR (400 MHz, CDCl$_3$) δ 3.09 (t, J=4.8 Hz, 4H), 3.59 (t, J=4.8 Hz, 4H), 6.92-7.01 (m, 6H), 7.33-7.38 (m, 3H), 7.52 (dd, J=2.0, 6.8 Hz, 2H).

Step 2

1-[4-(4-Thiophen-3yl-phenoxy)-phenyl]-piperazine hydrochloride: The title compound (0.045 g, 68%) was prepared by reacting the compound (0.095 mg, mmol) from step one with 2 N HCl in ether (2 mL) by using the procedure described in step 2 of Example 4: MS (ESI) m/z 337 (M+H); $^1$H NMR (400 MHz, DMSO-d$_6$). δ 3.22 (br, 4H), 3.34 (t, J=4.8 Hz, 4H), 6.96 (dd, J=2.0, 6.8 Hz, 2H), 7.00 (d, J=9.6 Hz, 2H), 7.05 (d, J=9.4 Hz, 2H), 7.50 (dd, J=1.2, 5.2 Hz, 1H), 7.62 (dd, J=2.8, 5.2 Hz, 1H), 7.69 (dd, J=6.8 Hz, 2H), 7.77 (dd, J=1.2, 2.8 Hz, 1H), 9.17 (br, 1H). Anal. Calcd for C20H20N2OS.2.4HCl: C, 56.66; H, 5.33; N, 6.61; S, 7.56. Found: C, 55.88; H, 5.41; N, 6.41; S, 7.53.

Example 24

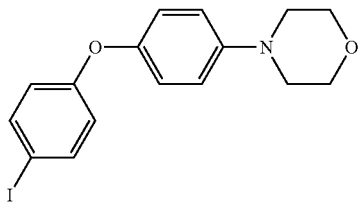

4-[4-(4-Iodo-phenoxy)-phenyl]-morpholine: The title compound (0.36 g, 99%) was prepared from 4-iodopheyl ether (0.42 g, 1 mmol) and morpholine (0.087 g, 1 mmol) in the presence of Pd$_2$(dba)$_3$ (0.027 g, 0.03 mmol), P$^t$Bu3 (0.058 g. 0.28 mmol) and NaO-t-Bu (0.095 g, 1 mmol) in toluene by using the procedure described in step 1 of Example 17: MS (ESI) m/z 382 (M+H); $^1$H NMR (400 MHz, CDCl$_3$) δ 3.12 (t, J=4.8, 4H), 3.87 (t, J=4.8 Hz, 4H), 6.69-6.72 (m, 2H), 6.89-6.92 (m, 4H), 7.55-7.57 (m, 2H).

Example 25

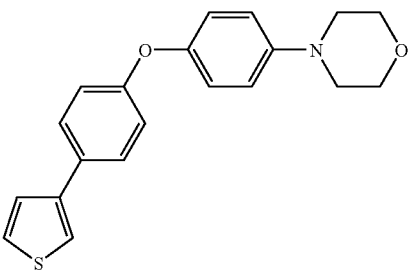

4-[4-(4-Thiophen-3-yl-phenoxy)-phenyl]-morpholine: The title compound (25 mg, 35%) was prepared by treating 4-[4-(4-Iodo-phenoxy)-phenyl]-morpholine (80 mg, 0.21 mmol) from Example 24 with thiophene-3-boronic acid (35 mg, 0.25 mmol) in the presence of 10% Pd/C (10 mg), potassium carbonate (87 mg, 0.68 mmol), 2-propanol (4 mL) and water (0.4 mL) by using the procedure described in step 2 of Example 16: MS (ESI) m/z 338 (M+H); $^1$H NMR (400 MHz, CDCl$_3$) δ 3.13 (t, J=4.8 Hz, 4H), 3.87 (t, J=4.8 Hz, 4H), 6.91-7.01 (m, 6H), 7.34-7.38 (m, 3H), 7.51-7.53 (m, 2H).

Example 26

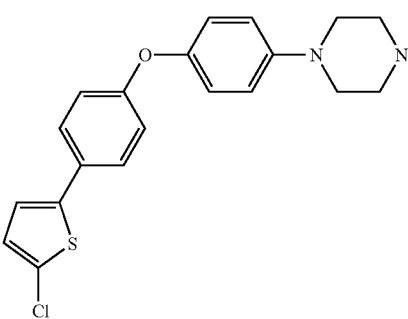

Step 1

1-[4-(4-Thiophen-3yl-phenoxy)-phenyl]-piperazine-1-carboxyliacid tert-butyl ester: The title compound (28 mg, 28%) was synthesized from 4-[4-(4-Iodo-phenoxy)-phenyl]-piperazine-1-carboxilic acid tert-butyl ester (100 mg, 0.21 mmol) from step 1 of Example 23, 5-chloro-thiophene-2-boronic acid (38 mg, 0.23 mmol), 10% Pd/C (10 mg), potassium carbonate (87 mg, 0.63 mmol) in 2-propanol (5 mL) and water (0.5 mL) by using the procedure described in Step 2 of Example 16: MS m/z 472 (M+H); $^1$H NMR (400 MHz, CDCl$_3$) δ 3.09 (t, J=5.4H), 3.59 (t, J=4.8 z, 4H), 6.86 (d, J=4.0 Hz, 1H), 6.91-6.99 (m, 7H), 7.40-7.43 (m, 2H).

Step 2

1-[4-(4-Thiophen-3yl-phenoxy)-phenyl]-piperazine hydrochloride: The title compound (17 mg. 66%) was prepared by treating the compound (28 mg, 0.059 mmol) from step 1 with 4 N HCl in dioxin using the procedure described in step 2 of Example 4: MS (ESI) m/z 372 (M+H); $^1$H NMR (400 MHz, DMSO-d$_6$) δ 3.22 (b, 4H), 3.34 (t, J=4.8 Hz, 4H), 6.94-6.97 (dd, J=2.0, 6.8 Hz 2H), 7.00-7.06 (m, 4H), 7.36 (d, J=4.0, 1H), 7.30 (d, 4.0, 1H), 7.58 (dd, J=2.0, 6.8 Hz, 2H).

(1) In Vitro Assay Testing Inhibitory Activity Against Purified Recombinant Human LTA4 Hydroase:

A human LTA4 hydrolase full-length cDNA clone (NM_000895) was purchased from OriGene Technologies (Rockville, Md.). The gene was amplified by polmerase chain reaction and transferred via pDONR201 into the bacterial expression vector pDEST17 by recombination (both plasmids from Invitrogen, Carlsbad, Calif.). The resulting construct was transformed into *Escherichia coli* BL21-AI (Invitrogen), and expression was induced by chemical induction with arabinose. The recombinant enzyme was purified by chromatography on a FPLC system (Amersham Biosciences, Uppsala, Sweden) using immobilized metal affinity chromatography (Ni-NTA Superflow, Qiagen, Hilden, Germany) and anion exchange chromatography (MonoQ HR 10/10, Amersham Biosciences).

The compounds of the invention were incubated in a series of dilutions with 200 nM of recombinant enzyme in assay buffer (100 mM Tris-HCl, 100 mM NaCl, 5 mg/ml fatty-acid free BSA, 10% DMSO, pH 8.0) for 10 min at room temperature to allow binding between LTA$_4$ hydrolase and the inhibitors. LTA$_4$ was prepared by alkaline hydrolysis of LTA$_4$ methyl ester (Biomol, Plymouth Meeting, Pa., or Cayman Chemicals, Ann Arbor, Mich.). A solution of 10 μg of the ester was dried under a nitrogen stream and redissolved in 60 μl of a solution of 80% aceton and 20% 0.25 M NaOH.

After incubation for 40 min at room temperature the resulting approximately 500 μM tock of LTA$_4$ was kept at −80° C. for no more than a few days prior to use.

Immediately before the assay, LTA$_4$ was diluted to a concentration of 10 μM in assay buffer (without DMSO) and added to the reaction mixture to a final concentration of 2 μM to initiate the enzyme reaction. After incubation for 120 sec at room temperature, the reaction was stopped by adding 2 volumes of chilled quenching buffer, containing acetonitril with 1% acetic acid and 225 nM LTB$_4$-d$_4$ (Biomol). The samples were then kept at 4° C. over night to complete protein precipitation and centrifuged for 15 min at 1800 g. LTB$_4$ formed was measured by LC-MS/MS using LTB$_4$-d$_4$ as an internal standard and an external LTB$_4$ standard (Biomol) as reference. Briefly, the analyte was separated from LTB$_4$ isomers formed by spontaneous hydrolysis of LTA$_4$ using isocratic elution (modified protocol from Mueller et al. (1996), J. Biol. Chem. 271, 24345-24348) on a HPLC system (Waters, Milford, Mass.) and analyzed on a tandem quadrupole mass spectrometer (Waters). MRM transitions followed on 2 channels were 335.2>195.3 (LTB$_4$) and 339.2>197.3 (LTB$_4$-d$_4$). Based on the amounts of LTB$_4$ found at each inhibitor concentration, a dose-response curve was fitted to the data and an IC$_{50}$ value was calculated.

(2) Ex Vivo Assay Testing Inhibitory Activity in Human Whole Blood after Stimulation with Calcium Ionophor:

Human blood was collected in heparin-containing Vacutainer tubes. For each sample, 200 μl of blood were dispensed into a pre-warmed plate and 188 μl of RPMI-1640 medium (Invitrogen) containing 20 μg/ml Indomethacin (Sigma, St. Louis, Mo.) were added. Then 4 μl of a series of compound dilutions (in DMSO) were added, followed by a 15 min incubation at 37° C. with gentle shaking. After that, blood samples were stimulated by adding Ionomycin (Calbiochem) to a final concentration of 20 μM.

After another incubation at 37° C. for 30 min, samples were centrifuged for 5 min at 1800 g and 4° C. Supernatants were taken and LTB$_4$ concentrations were determined using a commercially available enzyme-linked immunoassay (R&D Systems, Minneapolis, Minn.) according to the manufacturer's instructions. Results obtained for different concentrations of hydrolase inhibitor were then used to fit a dose-response curve and calculate an IC$_{50}$ value.

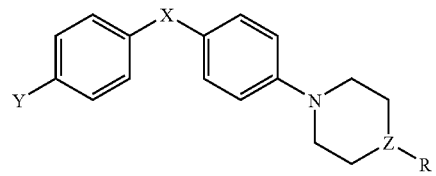

| Example | X   | Y | Z | R           | IC50 (μM)(hLTA4H) |
|---------|-----|---|---|-------------|-------------------|
| 1       | NH  | H | N | (CH2)2CO2CH3 | Q |
| 2       | NH  | H | N | (CH2)2CO2H   | Q |
| 3       | NH  | H | N | (CH2)3CO2H   | B |
| 4       | CH2 | H | N | H            | A |
| 5       | CH2 | H | N | (CH2)3CO2CH3 | A |
| 6       | CH2 | H | N | (CH2)3CO2H   | A |
| 7       | CH2 | H | N | (CH2)2CO2H   | A |
| 8       | O   | H | N | H            | A |
| 9       | O   | H | N | (CH2)3CO2H   | A |
| 10      | O   | H | N | (CH2)2CO2H   | Q |
| 11      | O   | H | N | CH2CO2H      | Q |

-continued

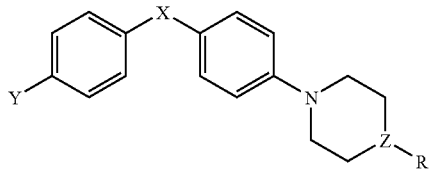

| Example | X | Y | Z | R | IC50 (μM)(hLTA4H) |
|---|---|---|---|---|---|
| 12 | O | H | CH | NH2 | B |
| 13 | O | H | CH | NHCH2CO2H | Q |
| 14 | O | I | N | H | A |
| 15 | O | I | N | (CH2)3CO2H | A |
| 16 | O | 3-thiophenyl | N | (CH2)2CO2H | A |
| 17 | O | OCH3 | N | H | B |
| 18 | O | CH3 | N | H | A |
| 19 | OCH2 | H | N | H | Q |
| 20 | O | CF3 | N | H | A |
| 21 | O | H | N | COCH3 | A |
| 22 | O | H | CH2 | NHCOCH3 | Q |
| 23 | O | 3-thiophenyl | N | H | A |
| 24 | O | I | O | — | A |
| 25 | O | 3-thiophenyl | O | — | A |
| 26 | O | 2(2-chloro thiophenyl) | NH | H | B |

A = <5 uM, B = 5–20 uM; C = 20–100 uM; Q = the compound was tested and found to be an inhibitor but no IC50 was determined.

We claim:

1. A compound of formula:

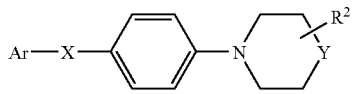

wherein

Ar is selected from the group consisting of phenyl, and phenyl substituted with from one to three substituents independently selected from the group consisting of halogen, loweralkyl, loweralkoxy, fluoroloweralkyl, 5-membered heteroaryl, and 5-membered heteroaryl substituted with halogen;

X is O;

$R^2$ is selected from the group consisting of H, loweralkyl, and —Z—W;

Y is

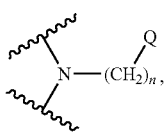

wherein the wavy lines indicate ring bonds;

Q is —OH or —COOH;

n is selected from 1, 2, 3, 4, 5, 6, 7, 8, 9 and 10, provided that n is not 1 when Q is —OH;

Z is $(CH_2)_{1-10}$; in which one or two $(CH_2)$ may optionally be replaced by a —O—, —$NR^{10}$—, or —C(=O)—, provided that said —O— —$NR^{10}$—, or —C(=O)— are separated by at least one —$(CH_2)_2$—;

$R^{10}$ is selected from the group consisting of H and lower alkyl;

W is selected from acyl, hydroxyl, carboxyl, and COOalkyl.

2. A compound according to claim 1 of formula:

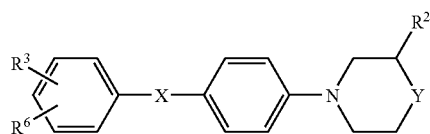

wherein each occurrence of $R^3$ or $R^6$ is selected from the group consisting of H, halogen, lower alkyl, fluoroloweralkyl, lower alkoxy, 5-membered heteroaryl, and 5-membered heteroaryl substituted with halogen.

3. A compound according to claim 2, wherein n is 1, 2 or 3 and Q is —COOH.

4. A compound according to claim 2, wherein $R^6$ is H and $R^3$ is in the para position.

5. A pharmaceutical composition comprising a pharmaceutically acceptable carrier and a therapeutically effective amount of at least one compound according to claim 1.

6. A compound according to claim 4, wherein X is O, and $R^3$ is 5-membered heteroaryl.

7. A compound according to claim 6, wherein said 5-membered heteroaryl is thiophene, n is 2, and Q is COOH.

8. A compound of formula:

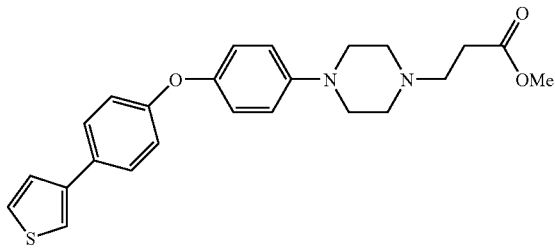

or a salt thereof.

9. A compound of formula:

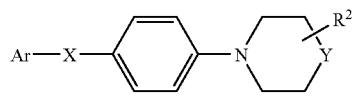

wherein

Ar is phenyl substituted with 5-membered heteroaryl, said heteroaryl optionally substituted with halogen;

X is O;

$R^2$ is selected from the group consisting of H, loweralkyl, and —Z—W;

Y is

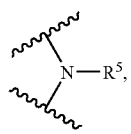

wherein the wavy lines indicate ring bonds;

$R^5$ is H;

Z is $(CH_2)_{1-10}$; in which one or two $(CH_2)$ may optionally be replaced by a —O—, —$NR^{10}$—, or —C(=O)—, provided that said —O—, —$NR^{10}$—, or —C(=O)— are separated by at least one —$(CH_2)_2$—;

$R^{10}$ is selected from the group consisting of H and lower alkyl; and

W is selected from acyl, hydroxyl, carboxyl, and COOalkyl.

10. A pharmaceutical composition comprising a pharmaceutically acceptable carrier and a therapeutically effective amount of a compound according to claim 9.

11. A compound of formula:

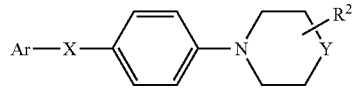

wherein

Ar is selected from the group consisting of phenyl, and phenyl substituted with from one to three substituents independently selected from the group consisting of halogen, loweralkyl, loweralkoxy, fluoroloweralkyl, 5-membered heteroaryl, and 5-membered heteroaryl substituted with halogen;

X is O;

$R^2$ is —Z—W;

Y is

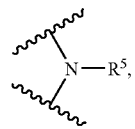

wherein the wavy lines indicate ring bonds;

$R^5$ is chosen from hydrogen and lower alkyl;

Z is $(CH_2)_{1-10}$; in which one or two $(CH_2)$ may optionally be replaced by a —O—, —$NR^{10}$—, or —C(=O)—, provided that said —O—, —$NR^{10}$—, or —C(=O)— are separated by at least one —$(CH_2)_2$—;

$R^{10}$ is selected from the group consisting of H and lower alkyl; and

W is selected from acyl, hydroxyl, carboxyl, and COOalkyl.

12. A compound according to claim 11 of formula:

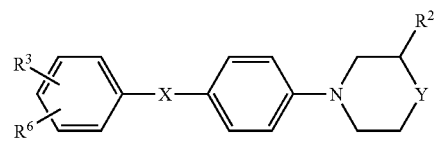

wherein each occurrence of $R^3$ or $R^6$ is selected from the group consisting of H, halogen, lower alkyl, fluoroloweralkyl, lower alkoxy, 5-membered heteroaryl, and 5-membered heteroaryl substituted with halogen.

13. A compound according to claim 12, wherein $R^6$ is H and $R^3$ is in the para position.

14. A compound according to claim 13, wherein $R^3$ is a 5-membered heteroaryl.

15. A pharmaceutical composition comprising a pharmaceutically acceptable carrier and a therapeutically effective amount of at least one compound according to claim 11.

16. A compound according to claim 14, wherein said 5-membered heteroaryl is thiophene, Z is —$(CH_2)_2$—, and W is carboxyl.

17. A compound of formula:

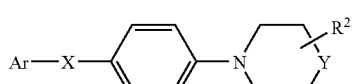

wherein $Ar^1$ is phenyl substituted with from one to three substituents independently selected from the group consisting of halogen, loweralkyl, loweralkoxy, fluoroloweralkyl, 5-membered heteroaryl, and 5-membered heteroaryl substituted with halogen;

X is O;

Y is

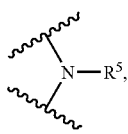

wherein the wavy lines indicate ring bonds;

$R^5$ is —Z—W,

Z is $(CH_2)_{1-10}$; in which one or two $(CH_2)$ may optionally be replaced by a —O—, —$NR^{10}$—, or —C(=O)—, provided that said —O— —$NR^{10}$—, or —C(=O)— are not at the point of attachment to nitrogen and are separated by at least one —$(CH_2)_2$—;

$R^{10}$ is selected the group consisting of H and lower alkyl; and

W is selected from acyl, carboxyl and COOalkyl.

18. A compound according to claim 17 of formula:

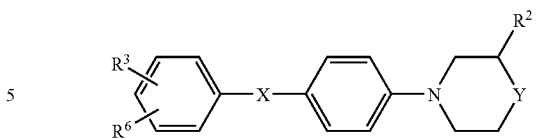

wherein each occurrence of $R^3$ or $R^6$ is selected from the group consisting of H, halogen, lower alkyl, fluoroloweralkyl, lower alkoxy, 5-membered heteroaryl, and 5-membered heteroaryl substituted with halogen; with the proviso that both $R^3$ and $R^6$ cannot be H.

19. A compound according to claim 18, wherein Z is $(CH_2)_{1-3}$.

20. A compound according to claim 18, wherein $R^6$ is H and $R^3$ is in the para position.

21. A pharmaceutical composition comprising a pharmaceutically acceptable carrier and a therapeutically effective amount of at least one compound according to claim 17.

22. A compound according to claim 20, wherein X is O, and $R^3$ is 5-membered heteroaryl.

23. A compound according to claim 22, wherein said 5-membered heteroaryl is thiophene, Z is —$(CH_2)_2$—, and W is carboxyl.

* * * * *

UNITED STATES PATENT AND TRADEMARK OFFICE
CERTIFICATE OF CORRECTION

PATENT NO. : 7,750,012 B2
APPLICATION NO. : 11/462278
DATED : July 6, 2010
INVENTOR(S) : Sandanayaka et al.

It is certified that error appears in the above-identified patent and that said Letters Patent is hereby corrected as shown below:

Claim 17, at Column 34, Line 55: Delete: " 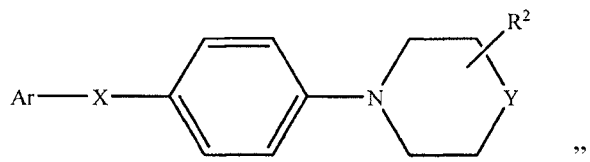 "

Insert: -- 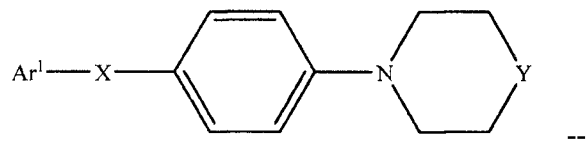 --

Claim 18, at Column 36, Line 5: Delete: " 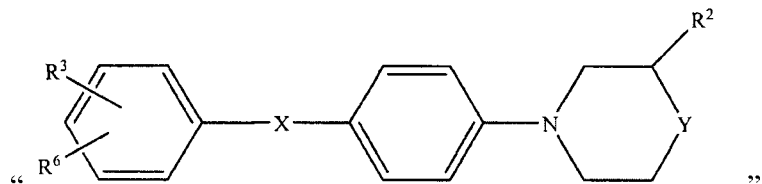 "

Insert: -- 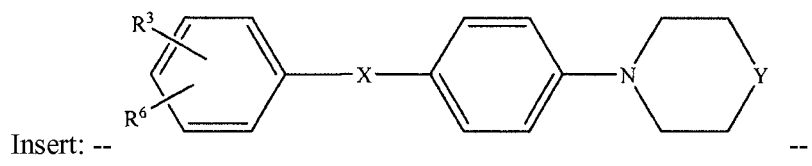 --

Signed and Sealed this
Third Day of May, 2011

David J. Kappos
*Director of the United States Patent and Trademark Office*